(12) United States Patent
Vaghefi et al.

(10) Patent No.: US 6,849,271 B2
(45) Date of Patent: Feb. 1, 2005

(54) MICROCAPSULE MATRIX MICROSPHERES, ABSORPTION-ENHANCING PHARMACEUTICAL COMPOSITIONS AND METHODS

(75) Inventors: Farid Vaghefi, Exton, PA (US); Martin F. Savitzky, Maple Glen, PA (US)

(73) Assignee: Verion, Inc., Lionville, PA (US)

( * ) Notice: Subject to any disclaimer, the term of this patent is extended or adjusted under 35 U.S.C. 154(b) by 243 days.

(21) Appl. No.: 10/274,225

(22) Filed: Oct. 18, 2002

(65) Prior Publication Data

US 2003/0157326 A1 Aug. 21, 2003

Related U.S. Application Data

(63) Continuation-in-part of application No. 09/844,064, filed on Apr. 27, 2001, now Pat. No. 6,544,646.
(60) Provisional application No. 60/330,232, filed on Oct. 18, 2001, and provisional application No. 60/389,530, filed on Jun. 18, 2002.

(51) Int. Cl.⁷ ............................. A61K 9/56; B32B 15/02
(52) U.S. Cl. ....................... 424/459; 264/4.3; 264/4.32; 264/4.4; 264/4.7; 264/13; 428/402.24; 428/403; 424/457; 424/458; 424/460; 424/461; 424/462; 424/489

(58) Field of Search ................. 264/4.3, 4.32, 264/4.4, 7, 13; 428/402.24, 403; 424/457, 458, 459, 460, 461, 489

(56) References Cited

U.S. PATENT DOCUMENTS

| 5,496,565 A | 3/1996 | Heinze et al. ............... 424/502 |
| 6,294,195 B1 | 9/2001 | Oshlack et al. ............. 424/457 |
| 2001/0018072 A1 | 8/2001 | Unger ......................... 424/484 |

*Primary Examiner*—Samuel A. Acquah
(74) *Attorney, Agent, or Firm*—Synnestvedt & Lechner LLP

(57) ABSTRACT

The present invention relates to microspheres, processes for the manufacture of said microspheres, pharmaceutical compositions comprising said microspheres, and sustained release methods of administering an effective pharmaceutical amount of a bioactive compound to a subject. The microspheres of the present invention comprise a water insoluble organic matrix comprising an interior region, throughout which are homogeneously dispersed a plurality of microcapsules consisting essentially of a core of bioactive compound coated with material containing charged organic groups and a surface region substantially free of said bioactive compound.

69 Claims, 10 Drawing Sheets

NIFEDIPINE, FASTED,
MEAN HUMAN PLASMA PROFILES

MICROCAPSULE MATRIX MICROSPHERES, ABSORPTION-ENHANCING PHARMACEUTICAL COMPOSITIONS AND METHODS

CROSS-REFERENCE TO RELATED APPLICATIONS

This application is a continuation-in-part of U.S. application Ser. No. 09/844,064, filed Apr. 27, 2001 now U.S. Pat. No. 6,544,646 and is also based on U.S. Provisional Applications Nos. 60/330,232, filed Oct. 18, 2001 and 60/389,530, filed Jun. 18, 2002.

FIELD OF THE INVENTION

The present invention relates to the field of pharmaceutical composition formulation and drug delivery methods. More specifically, the present invention relates to the development of drug formulations that enhance the amounts of drug absorbed by a subject across body membranes.

Bioactive compounds may be administered to a subject by transporting the compound across a variety of body membranes such as the dermal, nasal, pulmonary alveoli, rectal, eye, buccal and gastrointestinal (GI) membranes. The GI tract, particularly the small intestines, is the primary site for the oral absorption of nutrients and most bioactive agents. To provide for the amount of absorption that must take place in the small intestines, the surface area of the gastrointestinal membrane is enlarged as a result of the presence of villi and microvilli. Nonetheless, a bioactive compound must withstand degradation or deactivation by the various components of the luminal contents prior to its transfer from the intestinal lumen to the blood. Moreover, the compound may pass through several absorption barriers, such as the mucous layer and the intestinal brush-border membrane. Although many nutrients and compounds pass these barriers without degradation or deactivation easily, there are many nutrients and other bioactive agents for which these barriers are a significant challenge.

Many different types of bioactive agents, such as drugs, are normally poorly absorbed through the body's membranes, such as the GI tract and thus, have difficulty reaching the bloodstream systemically. There are several contributing factors to why poorly absorbable drugs have low absorption in the intestines after oral administration. First, these drugs may be very insoluble, or exhibit low permeability, or are generally unstable in an aqueous environment such as in gastric juices and small intestine fluids and be degraded by enzymes prior to being absorbed. According to the Biopharmaceutics Classification System of the Office of Pharmaceutical Science of the Food and Drug Administration, drug substances are classified in one of four classes: Class I—High Permeability, High Solubility; Class II—High Permeability, Low Solubility; Class III—Low Permeability, High Solubility; and Class IV—Low Permeability, Low Solubility. The Class III and IV drugs present a significant challenge to the pharmaceutical industry to formulate a composition for the preferred oral route of drug administration. Examples of low permeability drugs include amoxicillin, atenolol, furoseamide, hydrochlorothiazide, and L-methyldopa.

An exemplary class of low permeability drug is the third generation cephalosporins: these cephalosporins have been less effective when administered by routes other than parenteral to treat systemic bacterial infections. Specifically, administration of third generation cephalosporins is sometimes accomplished by infusion, but more typically by intravenous (i.v.) or intramuscular (i.m.) injections. The necessity of obtaining treatment through i.v. or i.m. injections is inconvenient, as such treatments often requires the services of doctors, nurses, or other trained technicians. Additionally, injections can be painful and cause undue physical and psychological stress to many patients.

Other examples of low permeable compounds include human hormones, neurotransmitters and other important biological compounds that have peptides as a substantial part of their molecular structures. Many diseases respond positively to raising the level of these peptide compounds in patients. Therapeutically effective amount of such biologically relevant peptides may be administered to patients in a variety of ways. However, as discussed further below, preferred oral administration is very difficult with this type of active compound. Proteolytic enzymes of both the stomach and intestines may degrade peptides, rendering them inactive before they can be absorbed into the bloodstream. Any amount of peptide that survives proteolytic degradation by proteases of the stomach (typically having acidic pH optima) is later confronted with proteases of the small intestine and enzymes secreted by the pancreas (typically having neutral to basic pH optima).

Salmon calcitonin is a peptide hormone which decreases uptake of calcium from bone. When used to treat bone-related diseases and calcium disorders (such as osteoporosis, Paget's disease, hypercalcemia of malignancy, and the like), it has the effect of helping maintain bone density. Many types of calcitonin have been isolated (human calcitonin, salmon calcitonin, eel calcitonin, elk calcitonin, porcine calcitonin, and chicken calcitonin). There is significant structural non-homology among the various calcitonin types. For example, there is only 50% percent identity between the amino acids making up human calcitonin and those making up salmon calcitonin. Notwithstanding the difference in molecular structure, salmon calcitonin may be used in the human treatment of the calcitonin-responsive diseases discussed above. Specific difficulties arising from the oral administration of a peptide like salmon calcitonin involve the relatively large size of the molecule, and the charge distribution it carries. This may make it more difficult for salmon calcitonin to penetrate the mucus along intestinal walls or to cross the intestinal brush border membrane into the blood. These additional problems may further contribute to limited bioavailability.

Protein and peptidyl pharmaceuticals are typically administered by injection or by nasal administration. Insulin is one example of a peptide pharmaceutical frequently administered by injection. However, injection and nasal administration are significantly less convenient than, and involve more patient discomfort than, oral administration. Often this inconvenience or discomfort results in substantial patient noncompliance with a treatment regimen. Thus, there is a need in the art for more effective and reproducible oral administration of peptide and protein pharmaceuticals like insulin, salmon calcitonin and others discussed in more detail herein.

REPORTED DEVELOPMENTS

Many efforts have been made to find improved compositions and methods for delivering small intestine absorbable drugs in the form of capsules, tablets, and/or suspensions that are not harmful to the body. Though ionic surfactants, such as sodium lauryl sulfate, or chelating agents such as EDTA, have been found to enhance intestinal absorption of such large molecules, large amounts of these substances are known to be harmful to the mucosal membrane.

Some technologies have shown some promise in providing compositions and methods of delivering third generation cephalosporins orally with increased intestinal absorption. In U.S. Pat. No. 4,525,339, beta-lactam antibiotics were shown to penetrate the mucosal membrane of the intestines by co-administering $C_2$-$C_{12}$ fatty acid mono-, di-, or triglycerides as an absorption enhancer. In U.S. Pat. No. 5,190,748, absorption of antibiotics (such as ceftriaxone) through oral and rectal routes is enhanced by utilizing a two-component absorption-enhancing system comprised of an ether of a $C_6$-$C_{18}$ alcohol and a polyoxyethylene glycol together with a second component selected from the group consisting of polyoxyethylene glycol $C_6$ to $C_{18}$ glyceride esters, $C_6$ to $C_{18}$ carboxylic acids or salts thereof, and esters of two or more $C_6$ to $C_{18}$ carboxylic acids, glycerol, and a polyoxyethylene glycol. Additionally, in U.S. Pat. No. 5,318,781, absorption of antibiotics (such as ceftriaxone) through oral and rectal routes is enhanced by utilizing a two-component absorption-enhancing system comprised of laureth-12, a second component salt of capric acid and caprylic acids, and a carrier. For optimum absorption, the antibiotic containing two-component enhancer system disclosed therein may include Miglyol-812, which is a caprylic/capric triglyceride. In U.S. Pat. No. 4,722,941, the permucosal absorption of various therapeutics, including antibiotics, is reported to be enhanced by the use of fatty acids and saturated or unsaturated fatty acid glycerides.

U.S. Pat. No. 6,248,360, discloses a pharmaceutical composition for oral delivery comprising (a) a biopolymer which is preferably swellable and/or mucoadhesive when hydrated and can be carrageenan, pectin, chondroitin sulfate, sodium alginate, and/or poly(methacrylic acid), (b) a poorly absorbable antibiotic contained within or ionically bound to the biopolymer; and (c) a metal cation ionically bound to at least one member selected from the group consisting of the biopolymer and the antibiotic. The patent suggests that that a charge interaction between the biopolymer, metal cation and antibiotic is necessary to have the system function effectively: consequently, this system may function only with ionizable antibiotics.

U.S. Pat. No. 6,086,918 discloses a system for the enhanced oral delivery of peptides, in particular salmon calcitonin, wherein a pharmaceutical peptide including composition comprises at pH-lowering agent; an absorption enhancer; and an enteric coating. However levels of calcitonin detected are a very small percentage of the drug administered.

Though each of these systems described and others are somewhat effective in delivering poorly absorbable antibiotics and peptides through the mucosal membrane after oral delivery, each have drawbacks that prevent their widespread use. It would be desirable to provide compositions and methods for administering significant amounts of low permeable drugs orally, using technology that is substantially independent of the ionizable characteristics of the drug, and thus, provide a general means that enables the administration of low permeable drugs conveniently and cost effectively to the patient, and that enhances the amount of low permeable drug absorbed by the absorption transport membrane.

SUMMARY OF THE INVENTION

The present invention relates to microspheres, processes for the manufacture of said microspheres, pharmaceutical compositions comprising said microspheres, and sustained release methods of administering an effective pharmaceutical amount of a bioactive compound to a subject. The microspheres of the present invention comprise a water insoluble organic matrix comprising an interior region, throughout which are homogeneously dispersed a plurality of microcapsules consisting essentially of a core of bioactive compound coated with material containing charged organic groups and a surface region substantially free of said bioactive compound. The microsphere capsules contain cores having a diameter of less than about ten microns.

The microspheres of the present invention are prepared by a process comprising spraying, into a chilling zone, a flowable dispersion of bioactive micron sized organic particles containing charged organic moieties in a water insoluble fluid matrix, under conditions that form droplets of said dispersion, and maintaining the fluidity of, and charge on, said droplets for a time sufficient to distribute homogenously said particles within said droplets, and solidifying said droplets into said microspheres.

The afore-described microspheres are employed in the present pharmaceutical composition invention. The pharmaceutical composition invention comprises microspheres, each having a surface and an interior, and comprising a pharmaceutically acceptable water insoluble organic matrix material, within which interior are distributed water-dispersable capsules consisting essentially of a core of a bioactive compound in a pharmaceutically effective amount, and having a coating consisting essentially of an organic material having multiple charged groups, wherein said capsules are distributed homogenously within said microsphere. The composition may include the microspheres as a multi-particulate system filled in a capsule, such as a gelatin capsule or the like, or in a compressed tablet along with additional tableting excipients.

Another aspect of the present pharmaceutical composition comprises microspheres having a structure of an outer surface, and an interior region, said structure of said microspheres comprising a matrix of pharmaceutically acceptable water insoluble material, and particles of a hydrophobic bioactive compound coated with a pharmaceutically acceptable charged hydrophilic material, which particles are distributed homogenously within said interior region and are absent in the surface region.

A further aspect of the present invention relates to a method for increasing the absorption of a pharmaceutically active compound by a subject to which said compound is administered, comprising administering to said subject a sustained-release composition comprising an effective pharmaceutical amount of the present pharmaceutical composition.

These and further aspects of the present invention are described in more detail in the following sections.

DETAILED DESCRIPTION

Figure 1:
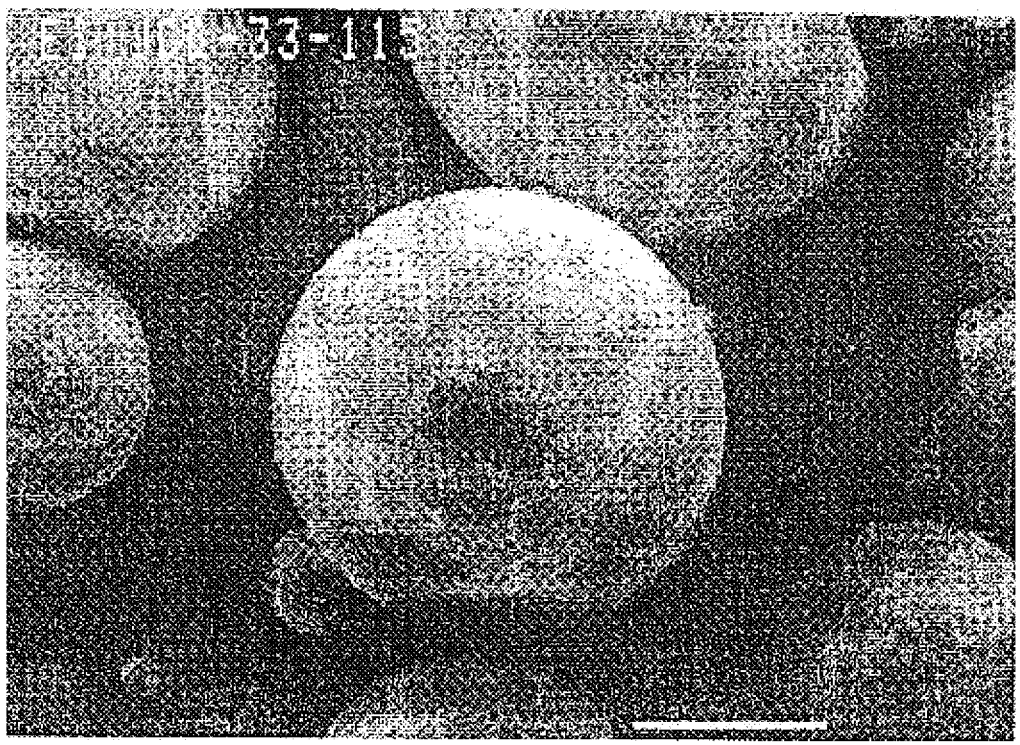
FIG. 1. is a scanning electron micrograph of the microspheres prepared in Example 1.
Figure 2:
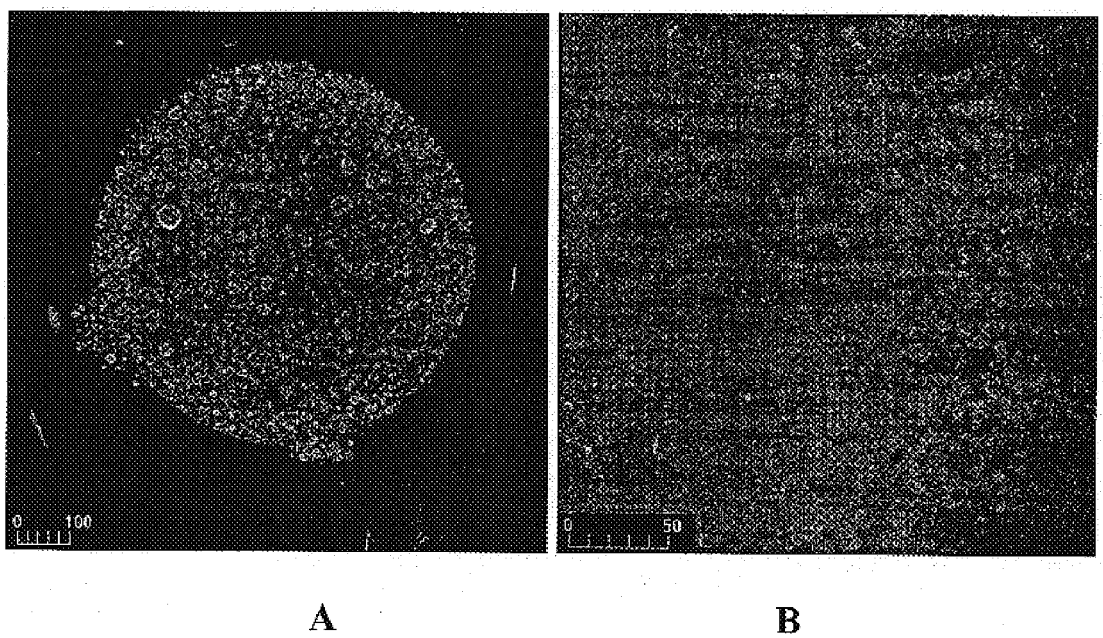
FIG. 2. is a confocol laser fluorescence micrographs focused within the interior of microspheres of Example 1 (24% nifedipine, 3 passes of pressure treatment) showing individual fluorescent particles of nifedipine/CMC microspheres distributed along a hemispherical plane. The photomicrograph (A) includes a scale marker of 100 microns and the photomicrograph (B) has a scale marker of 50 microns.
Figure 3:
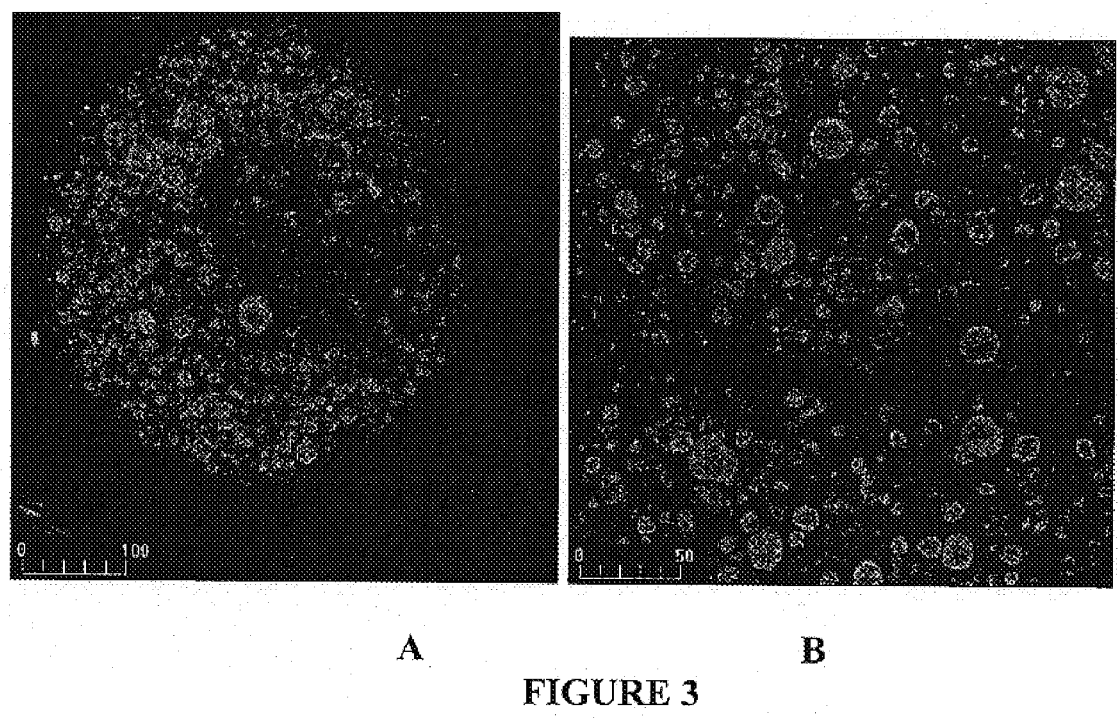
FIG. 3. is a confocol laser fluorescence micrograph of the interior of a microsphere prepared in accordance with the procedure of Example 1 except that the nifedipine percentage is 10% by weight. The photomicrograph (A) includes a scale marker of 100 microns and the photomicrograph (B) has a scale marker of 50 microns.
Figure 4:
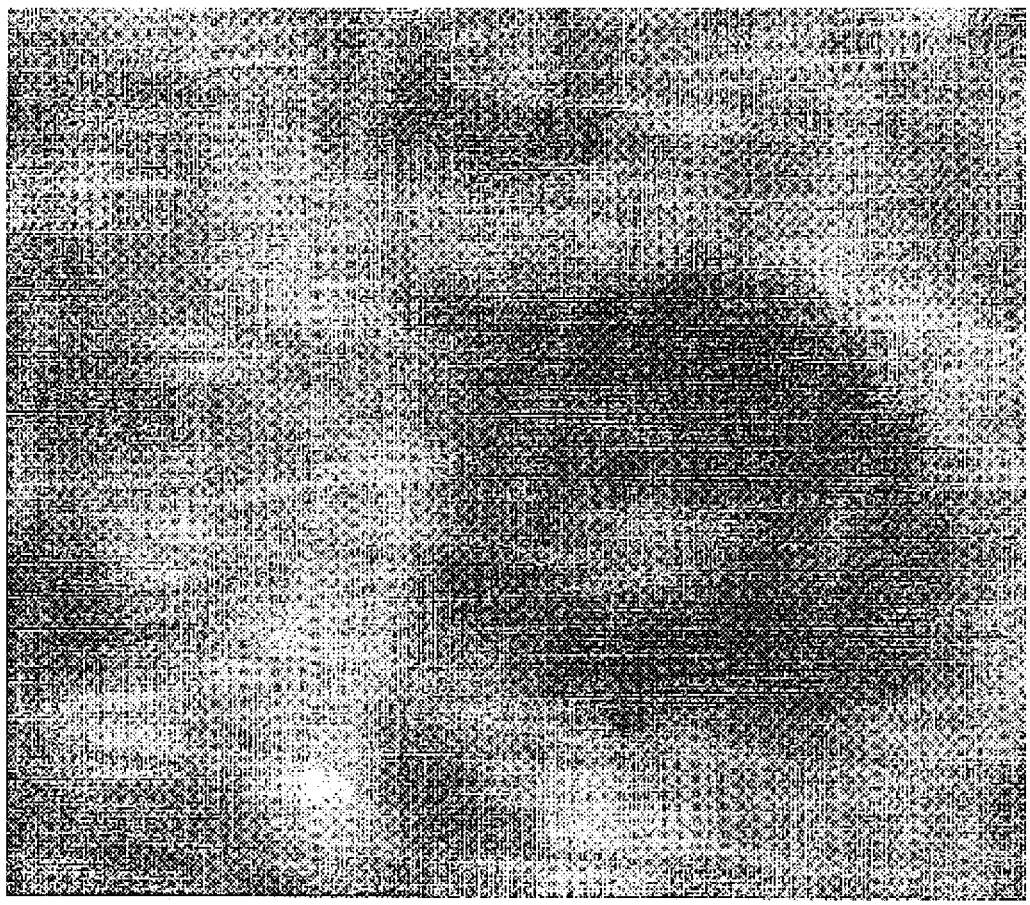
FIG. 4. is a high magnification confocol laser optical photomicrograph of a hemispherical section of a microsphere prepared according to Example 2. The microsphere matrix including the microcapsules of nifedipine is shown.
Figure 5:
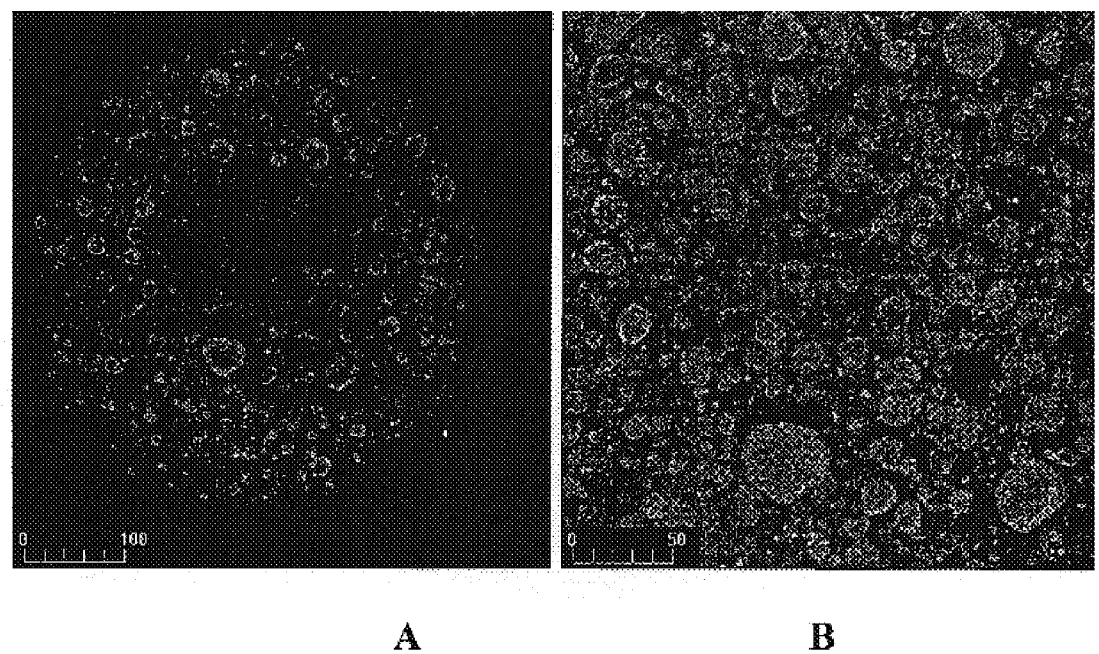
FIG. 5. is a confocol laser fluorescence micrograph of the interior of a microsphere prepared in accordance with the procedure of Example 1 except that the matrix no pressure treatment was used. The larger microcapsules not comminuted by the abrupt pressure process used to prepare the microspheres depicted in FIGS. 2 and 3 are visible. The photomicrograph (A) includes a scale marker of 100 microns and the photomicrograph (B) has a scale marker of 50 microns.
Figure 6:
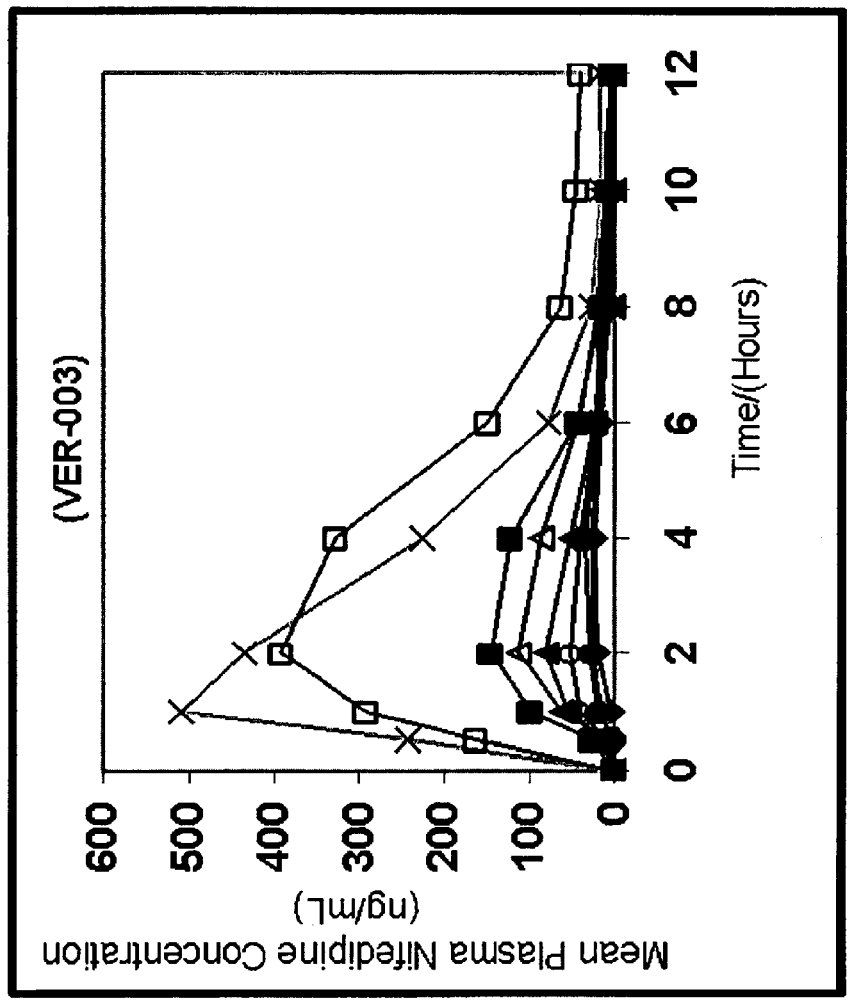
FIG. 6. is a graph showing the mean plasma levels in rats of eight nifedipine formulations containing the same percentage of nifedipine, prepared in the same way except for varying amounts of NaCMC and cetyl alcohol. The six graphs showing the lowest levels of nifedipine plasma levels do not include NaCMC but have increasing levels of nifedipine in the plasma as a function of increasing amounts of cetyl alcohol. The two formulations showing the highest plasma levels include NaCMC and differ only in the presence or absence of cetyl alcohol.
Figure 7:
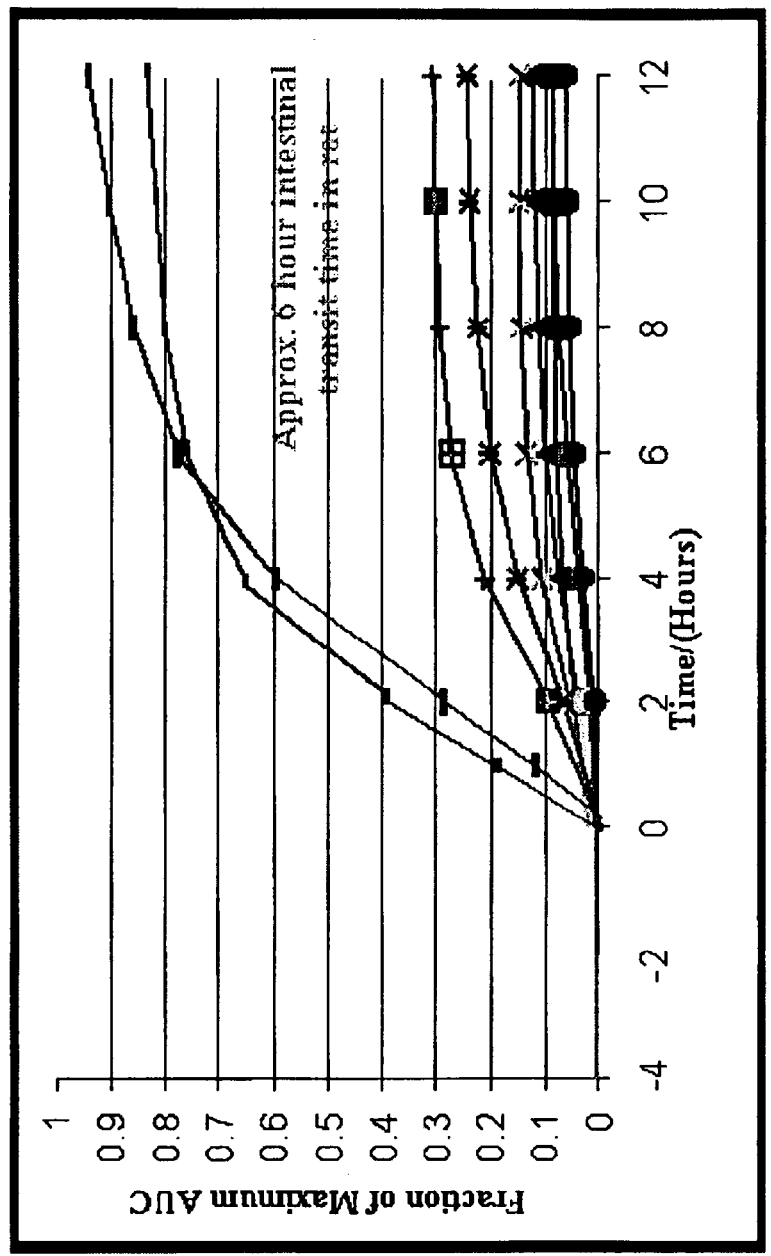
FIG. 7. is a graph showing deconvulated data presented in FIG. 6, assuming a half-life in rats of nifedipine of 15–25 minutes. The absorption rates have been normalized to the maximum AUC achieved by the formulations.

The term "capsules" or "encapsulated particles" as used herein refers to particles that have a shell component and a core component wherein the shell component at least partially encloses the core component, which may be a single core or comprise numerous cores dispersed among the shell material as a matrix.

The term "microsphere" as used herein is a particle in a variety of shapes including spherical, elongated or even rod-like spherical shape, and that has a diameter of the order of about 5–5000 microns, and most preferably from about 10 to 1000 microns, and most preferably from about 20 to about 800 microns. The preferred microspheres are substantially spherical in shape The term "microcapsule" as used herein is a capsule as defined hereinabove, which capsule has a core diameter of the order of about 0.01 to less than about 20 microns, and most preferably from about 0.1 to about 15 microns, and most preferably from about 0.2 to about 5 microns.

The core bioactive compound material may be a solid particle, in crystalline or amorphous form, a fluid, liquid or gas. Any material that retains its shape and configuration, within the liquid medium during processing can be used. The bioactive cores are preferably organic and may be water soluble, sparingly soluble in water or water insoluble.

The microcapsules are encapsulated, coated, or surrounded by a material that preferably contains organic groups that exhibit a dipole moment. Most preferably the material is an anionic or cationic polymer. The preferred polymers consist essentially of a polymeric backbone to which a plurality of pharmaceutically acceptable alkyl carboxylic acid, sulfate, ammonium or phosphate are covalently bonded. Most preferably, these polymers comprise the pharmaceutically acceptable acid addition salts thereof.

Exemplary polymers are ionizable and include poly (acrylic)- and/or poly(methacrylic) acid (e.g., Carbopol, Carhomer), poly(methylvinyl ether/maleic anhydride) copolymer, and their mixtures and copolymers; acidic synthetically modified natural polymers, such as carboxymethylcellulose (CMC); acidic normaturally occurring polymers, preferably having at least one acidic group per four repeating or monomeric subunit moieties such as alginic acid, hyaluronic acid, pectin, pectic acid, carrageenean, arabinogalactose, chondroitin sulfate, dextran, galactomannan (guar gum), gum tragacanth, karaya gum, xanthan gum and xylan, basic amine-bearing polymers such as chitosan. The ionizable polymers may be present as salts.

A preferred class of polymer materials contains a backbone that is selected from the group consisting of cellulose, hemicellulose, galactose polymer and 3,6-anhydrogalactose copolymers. Most preferred materials comprise polymers that are a pharmaceutically acceptable monovalent salt of an anionic polymer selected from the group consisting of carboxyalkylcellulose, pectinate, carrageenenate, xanthanate and alginate. The most preferred salts are alkali metal or ammonium salt. A particularly preferred polymer salt is an alkali metal or ammonium salt of carboxymethylcellulose, pectin or pectic acid, or mixtures thereof.

A special embodiment of polyanionic polymer is a pharmaceutically acceptable monovalent salt of a carboxyalkylcellulose. Preferred monovalent cations to form such salts include ammonium or alkali metal cations. Particularly preferred metal cations include lithium, sodium and potassium.

A particularly useful polymer is sodium carboxymethylcellulose (CMC), available in refined grades. Refined CMC is a cellulose ether, produced by reacting alkali cellulose with sodium monochloroacetate. The reaction is controlled in such a way that a predetermined substitution by sodium carboxymethyl groups (—CH2COONa) is obtained. This is expressed as degree of substitution (DS), or the average number of sodium carboxymethyl groups per anhydroglucose unit on the cellulose chain.

Formula 1 below illustrates the structural form of cellulose: on each anhydroglucose unit there are three OH (hydroxyl) groups which may be theoretically reacted

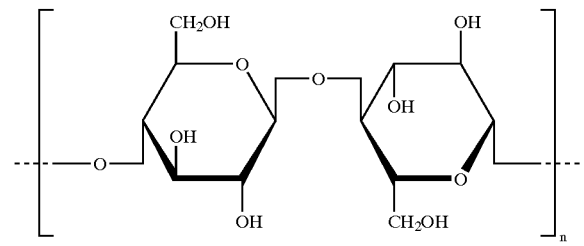

Formula 1

Formula 2 shows the same cellulose chain with a DS of 1.0. The substitution necessary to achieve optimum solubility and other desirable physical properties is less than three.

For example the most widely used types of BLANOSE brand of CMC exhibits a substitution of approximately 0.7—commonly referred to as "7-type". Other CMC grades have a DS of approximately 0.9, these have been designated as "9-types".

Formula 2

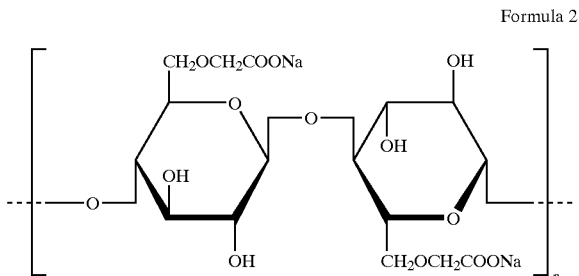

Idealized structure of Refined CMC, D.S. 1.0

The viscosity of CMC is controlled by varying the length of the basic cellulose chain. Aqualon® and Blanose™ cellulose gum, also known as sodium carboxymethylcellulose or CMC, is available in highly purified grades to meet the standards of the U.S. Food Chemicals Codex, EEC, and the Food and Agricultural Organization (FAO/WHO). These purified grades meet the standards set by the U.S. Code of Federal Regulations, Title 21, Section 182.1745—Substances that are generally recognized as safe (GRAS). Aqualon/Blanose food-grade cellulose gum meets these requirements. The pH of 1% solutions of refined CMC useful in the present invention can range from 6.5 to about 8.5., and the degree of substitution can range from 0.65 to about 0.95. Preferred CMC polymers useful in the present invention have a substitution range of from 0.65 to about 0.9.

Another particularly preferred anionic polymer is pectin or pectic acid, which is a polymer of galacturonic acids that may be partially esterified, and that are represented by the structures depicted in Formula 3 below.

Pectins are available with high methoxy content ("HM") or low methoxy content ("LM"). The salts of the LM pectins are particularly preferred.

The preferred water-soluble polyanionic polymers are of low viscosity to permit the efficient encapsulation of the bioactive compound. A preferred method of encapsulation involves treatment of a mixture of bioactive compound dispersed in the water insoluble matrix material with high-pressure forces. Admixture of the bioactive compound and the charged hydrophilic material may be achieved in any number of ways. A preferred method is spray drying, which is facilitated by a low viscosity polymeric material. Preferred shell materials are of low viscosity and non-gelling during processing. The preferred viscosity of the hydrophilic polymer of use in the present invention is from about 25 to about 1000 cps, more preferably from about 25 to about 800 cps, most preferably from about 25 to about 200 cps. A special embodiment of the present invention uses a CMC grade having a viscosity of about 25 to about 50 cps. The aforesaid viscosity values are obtained using a Brookfield LVT viscometer at 25 degrees C., at a concentration of 1–2 wt %, using spindle 1, 2 or 3 and a rate of 30–60 rpm. The most preferred grades of CMC available from Hercules Chemical Company are Blanose grades 7L2p, 7LF, 7M2F, 7M8SF and 7MF.

A special embodiment of the hydrophilic polymer is its ability to form a cross-linked polymeric network or structure upon admixture with multivalent cations, for example, calcium, magnesium, or iron+3. The multivalent cation may be added to the microsphere composition in the form of the salt of a bioenhancer, such as an anti-oxidant, for example citric acid, ascorbic acid, tocopherol phosphate, ascorbic phosphate, and the like.

A particularly preferred structural aspect of the present microspheres is a surface region that is substantially free of said material. Another particularly preferred aspect of the present microspheres is that the surface region is substantially free of the bioactive compound.

The microsphere comprises a water insoluble matrix of organic material that is resistant to dissolution or acidic Formula 3

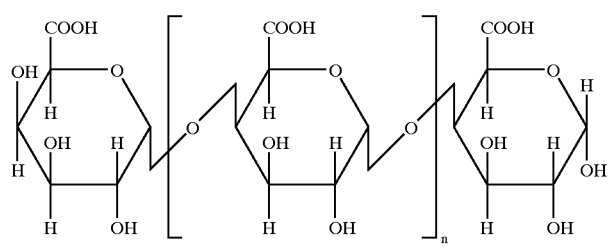

Pectic Acid

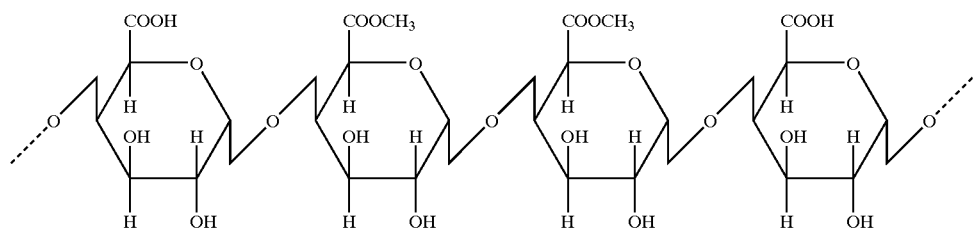

Pectin Molecule degradation at pH levels found in the stomach, which pH is lower than about 4. The organic matrix material comprises a member selected from the group consisting of triglycerides, hydrogenated vegetable oils, a wax or a mixture of waxes, triglycerides, polyalkoxyalkylethers, polyalkoxyalkylesters and water insoluble partially degraded proteins. A preferred class of materials includes fats such as triglycerides and hydrogenated triglycerides derived from natural sources, and waxes. A particularly preferred class fats and waxes include the partially digestible and indigestible waxes, such as materials prepared from, for example, beeswax, paraffin, and carnauba waxes.

Particularly preferred water insoluble materials comprise a wax or a mixture of waxes. The water insoluble organic material preferably is a naturally derived or synthetically produced wax material, which may comprise a single chemical component or a mixture thereof. A preferred wax is a partially digestible or indigestible wax. The wax material is most preferably a triglyceride or a mixture of triglycerides such as is found in hydrogenated or partially hydrogenated vegetable oils.

The term "wax" as used herein is intended to have as broad a meaning as possible and contemplates organic ester and waxy compounds derived from animal, vegetable, and mineral sources including modifications of such compounds from all three sources in addition to synthetically produced materials having similar properties. Examples of some of the waxes that may be used either alone or in combination with this invention include glyceryl tristearate, glyceryl distearate; Dynasan™ 110, 114, 116, 118; Sterotex™; canola wax/oil; cotton flakes; soya flakes; castor wax; rapeseed wax; beeswax; carnauba wax; candelilla wax; microwax (petroleum boler™ Wax 1014 based); Dritex C™; special fat™ 42, 44, 168 t; Be Square™ Wax #195a; Be Square™ Wax #195w; Energybooster™; Astor™ Wax 180; Astor™ Wax 150; and polyethylene.

Fats are the commonly used class of waxes and preferred in particular embodiments of the present invention are known as the triglycerides. In nature, triglycerides are usually found in complex mixtures. Depending upon the source of the triglyceride, whether animal or plant, the triglyceride may be formed from shorter or longer carboxylic acids which may in turn be either saturated or unsaturated. Triglycerides formed from shorter chain, unsaturated carboxylic acids, as a rule, melt at a lower temperature than triglycerides formed from longer-chain, saturated acids. In most cases, triglycerides are formed of more than one type of carboxylic acid. Further, the physical characteristics of a triglyceride (such as whether it exists as a liquid or solid at room temperature) are determined not only by which carboxylic acids were incorporated by esterification but also in which of the glyceryl hydroxy positions a given carboxylic acid was incorporated. Thus, animal triglycerides differ from plant triglycerides not so much in the overall ratios of saturated to unsaturated acids or of acids of given lengths, but rather in which of the three hydroxy positions in the glyceryl molecule unsaturated acids are to be found. Also, typically, naturally occurring triglyceride waxes, which are solid at room temperature, do not display a single sharp melting point because of the wide range of triglycerides present in most natural products.

Triglyceride waxes may be obtained commercially with a choice of chain length of the carboxylic acids that form the triglycerides, as well as a choice of purity grades. Commercial preparations of triglycerides start with natural products in which a number of different triglycerides are associated with each other. Processing not only saturates the acid substituents but also reduces the variety of triglycerides in the final material. The method and apparatus of this invention may be clearly demonstrated using the monoacid triglyceride, glyceryl tristearate ("tristearin") formed by the esterification of 18-carbon stearic acids with all three hydroxy groups of glyceryl. Stearic acid is a fully saturated carboxylic acid. One suitable commercial grade of tristearin is a product having the trademark "Dynasan™ 118" which is manufactured by Dynamit Nobel, a subsidiary of Hulls America. Dynasan™ 118 is a highly purified material from a vegetable source that contains relatively few triglyceride molecules that have esterified acids of different lengths. Similar, although somewhat less pure triglyceride materials are also commercially available under the trademark Sterotex™. As it is supplied by the manufacturer, Dynasan 118 is a white microcrystalline powder crystallized in the beta form, the DSC of which exhibits a single endothermic peak centered at approximately 72.degree. C. indicating that only a single polymorphic form is present with a melting point within the melting point temperature range of the beta form. Other preferred triglyceride waxes include Dritex C, a hydrogenated cottonseed oil wax, and BF117 (Bakers Flake 117) now sold as Shurset 117, partially hydrogenated soybean oil, both of which are sold commercially by AC Humko.

The matrix composition comprises from 0 to about 50-wt % of a water insoluble polysaccharide, a polyethylene glycol or glycol ether, or a second indigestible wax, based on the weight of the total material.

A most preferred matrix composition comprises from about one to about 50 wt % of an aliphatic alcohol having from about 8 to about 20 carbon atoms, based on the weight of the total material. A particularly preferred alcohol is a fatty acid alcohol. Most preferred alcohols include stearyl alcohol and cetyl alcohol.

The preferred water insoluble organic matrix material melts between about 120 degrees F. and about 225 degrees F., and preferably between about 125 and 189 degrees F., and most preferably between about 130 and about 160 degrees F. A single endothermic peak in the melting curve of the matrix material is preferred, although not required. A relatively sharp melting point peak is most preferred.

The preferred pharmaceutical compositions include microspheres that comprise a matrix of pharmaceutically acceptable water insoluble material, and particles of a bioactive compound coated with a pharmaceutically acceptable charged hydrophilic material. The particles in the microsphere are distributed homogenously within the interior of the microsphere and are absent from the surface.

The more preferred pharmaceutical compositions comprise a water insoluble matrix material that is insoluble and resistant to degradation in the acidic pH conditions of the stomach. Such preferred compositions comprise microspheres, the surface of which is wrapped in such water insoluble material, does not exhibit the bioactive material or charged hydrophilic material on its surface, and is hence essentially enteric in structure. Most preferred compositions include microspheres wherein such surface characteristics are integral to the microsphere structure and do not comprise a separate coating layer to achieve such surface conditions.

A further preferred aspect of the present invention uses a water insoluble matrix material comprising a pH insensitive material, which include, but are not limited to, ethylcellulose, cellulose acetate, vinyl acetate/vinyl chloride copolymers, acrylate/methacrylate copolymers, polyethylene oxide, hydroxypropyl methylcellulose, hydroxyethyl cellulose, hydroxypropyl cellulose, triglycerides, hydrogenated vegetable oils, triglyceride polyalkoxyalkylesters, fats, waxes and water insoluble partially-degraded proteins.

A most preferred water insoluble matrix material comprises at least one component that is pH insensitive and that is digestible by enzymes present in the mammalian intestinal tract, most preferably the human intestinal tract. This aspect of the present invention is particularly useful for preferred pharmaceutical compositions of the present invention, which are preferably administered by the oral or rectal routes.

A particularly preferred aspect of the pharmaceutical composition includes a pH insensitive material that comprises one or more components digestible by enzymes and/or dispersable by surfactants present in the small intestine. In this regard, such materials are most preferred if they are digestible by the lipases present in the small intestine. Preferred materials include lipase degradable fats, waxes, triglycerides, hydrogenated vegetable oils, and triglyceride polyalkoxyalkylesters.

A special embodiment of the present invention comprises a matrix material that include at least two components, wherein one component is digestible in the small intestine and a second component is indigestible in the small intestine. The digestible component may be a lipase-sensitive material, and is present in an amount from 100 percent by weight, to about 10 percent by weight based on the matrix material. A more preferred matrix composition comprises from about 5 to about 50 wt % of the digestible component, most preferably from 10 wt % to about 30 wt %, in combination with from about 95 wt % to about 50 wt %, and most preferably about 90 wt % to about 70 wt % of a small intestine indigestible or "lipase insensitive" component. Matrix compositions containing about 15 wt % to about 25 wt % of the digestible component are particularly preferred.

The small intestine indigestible or "lipase insensitive" component may be any material that is both pH insensitive and insensitive to the enzymes present in the gastrointestinal tract extending from the mouth until the cecum of the large intestine. Exemplary materials include, but are not limited to a water insoluble polysaccharide, a polyethylene glycol or glycol ether, or an indigestible wax or long chain aliphatic fatty acid ester. A particular embodiment of this component comprises a material that is digestible by enzymes present in the large intestine.

The incorporation into the matrix material of a polar component enhances the ability of the water insoluble or slightly water-soluble organic bioactive compound to be released. A preferred embodiment of the pharmaceutical composition comprises a matrix material that comprises from 2 to about 50 wt %, most preferably from 10 wt % to about 30 wt %, of an absorbable aliphatic alcohol having from about 8 to about 20 carbon atoms, in combination with small intestine indigestible or "lipase insensitive" component in an amount of from about 98 wt % to about 50 wt %, and most preferably about 90 wt % to about 70 wt %, based on the weight of the total material. A more preferred embodiment includes from about 5 to about 25 wt %, and most preferably about 15 wt % to about 20 wt % of the aliphatic alcohol. Most preferred alcohols are fatty acid alcohols, the most preferred being cetyl alcohol and stearyl alcohol.

The water insoluble inorganic material is nontoxic to animals, particularly humans, in the amounts contemplated for administration, and are considered pharmaceutically acceptable to person skilled in the pharmaceutical formulation arts.

A further preferred aspect of the pharmaceutical composition comprises a hydrophilic material encapsulating said particles, which material comprises an anionic or cationic polymer. A particularly preferred polymer exhibits mucoadhesive properties. Preferred mucoadhesive polymers may be present within the microspheres a cross-linked or not cross-linked.

One aspect of the invention comprises a pharmaceutical composition, wherein said bioactive compound is hydrophobic, and hence the particles thereof are sparingly soluble to water insoluble. A further aspect comprises a pharmaceutical composition, wherein said bioactive compound is hydrophilic, and water-soluble.

In one preferred embodiment, the microspheres have a bioactive compound content in a range of about 10 to about 45% by weight, preferably about 20 to about 35% by weight.

Preferred microspheres of the present invention are capable of in vitro and in vivo release of about 70 to about 100 percent of the core material over a period of about 8 to about 14 hours, and most preferably about 12 hours. Another preferred composition is capable of in vitro and in vivo release of about 80 to about 100 percent of the core material over a period of about 20 to about 26 hours, preferably about 22 to about 25 hours, and most preferably about 24 hours.

The composition and method according to the present invention incorporate and deliver a bioactive compound, that can be a nutrient or a compound that exhibits a pharmaceutical effect on a subject to which the compound is administered. Such a nutrient or bioactive compound may exhibit low solubility or low permeability or both. One particular benefit of the present invention is its ability to deliver a bioactive compound that is from water soluble, to sparingly soluble in water to water-insoluble. Another aspect of the present invention is the ability to administer a bioactive compound that exhibits low permeability across the membrane of said subject to which said drug is administered. A special embodiment of the present invention is useful for the administration of a low permeable bioactive compound that is also from sparingly soluble in water to water-insoluble.

As mentioned above, drug substances are classified as follows:
  Class I—High Permeability, High Solubility
  Class II—High Permeability, Low Solubility
  Class III—Low Permeability, High Solubility
  Class IV—Low Permeability, Low Solubility The boundaries of these classes of drugs can be determined without undue experimentation by persons of ordinary skill in the art. The FDA publishes guidelines for these determinations. For example, a drug substance is considered highly soluble when the highest dose strength is soluble in $\leq 250$ ml water over a pH range of 1 to 7.5. A drug substance is considered highly permeable when the extent of absorption in humans is determined to be $\geq 90\%$ of an administered dose, based on mass-balance or in comparison to an intravenous reference dose.

The aforesaid solubility determination is achieved with a pH-solubility profile of the test drug in aqueous media with a pH range of 1 to 7.5, using the shake-flask or titration method, and an analysis by a validated stability-indicating assay. Dissolution is determined using USP apparatus I (basket) at 100 rpm or USP apparatus II (paddle) at 50 rpm, a dissolution media (900 ml): 0.1 N HCl or simulated gastric fluid, pH 4.5 buffer, and pH 6.8 buffer or simulated intestinal fluid.

The aforesaid permeability determination is achieved by measuring the extent of absorption in humans, or mass-balance pharmacokinetic studies, or absolute bioavailability studies. Intestinal permeability methods may comprise in vivo intestinal perfusions studies in humans, in vivo or in situ intestinal perfusion studies in animals; in vitro permeation experiments with excised human or animal intestinal tissue; or in vitro permeation experiments across epithelial cell monolayers.

The permeability classes of the following compounds are published by the FDA: Antipyrine (High); Caffeine (High); Carbamazepine (High); Fluvastatin (High); Ketoprofen (High); Metoprolol (High); Naproxen (High); Propranolol (High); Theophylline (High); Verapamil (High); Amoxicillin (Low); Atenolol (Low); Furosemide (Low); Hydrochlorthiazide (Low); Mannitol (Low); L-Methyldopa (Low); Polyethylene glycol (400) (Low); Polyethylene glycol (1000) (Low); Polyethylene glycol (4000) (Low); (Zero permeability marker)); and Ranitidine (Low).

The composition according to the present invention comprises a capsule consisting essentially of a core of bioactive compound in a pharmaceutically effective amount and a shell surrounding said core, said shell consisting essentially of an absorption-enhancing amount of pharmaceutically acceptable, water soluble, low-viscosity, charged polymer. The shell may comprise additional components. A preferred additional component is water, which may be present in the shell in an amount required to facilitate the introduction of additional ingredients into the shell. Such ingredients include water-soluble bioenhancers, such as anti-oxidants, and multivalent cations to effect cross-linking of the microcapsules. The shell may also contain small amounts of surfactant, preferably 0.01 to 0.5% w/w of the microcapsule such as ionic surfactants, including sodium lauryl sulfate or chelating agents such as EDTA. The preferred compositions of the present invention provide a highly stable and protective carrier vehicle for the core material, until activated to release the core material by means of one or more dissolution mechanisms The pharmaceutical composition of the present invention is contacted with a body membrane capable of absorbing said drug. The membrane to be contacted can be any body membrane through which a bioactive compound may be absorbed, including membranes of the gastrointestinal tract, nasal passages, rectum, pulmonary aveoli, eye or buccal cavity. A particularly preferred membrane is found within the gastrointestinal tract.

Most preferred oral compositions release the bioactive compound only after passing through the low pH environment of the stomach. Preferred embodiments of the present composition include release mechanisms programmed to deliver the bioactive compound in the small intestine, the large intestine or both. The location and timing of bioactive release is by design. The compositions of the present invention are capable of releasing an enhanced amount of bioactive compound and of increasing the bioavailability of said compound in a continuous, sustained and controlled release rate of the core material from the capsule.

Compositions that Release in the Small Intestine

Figure 10:
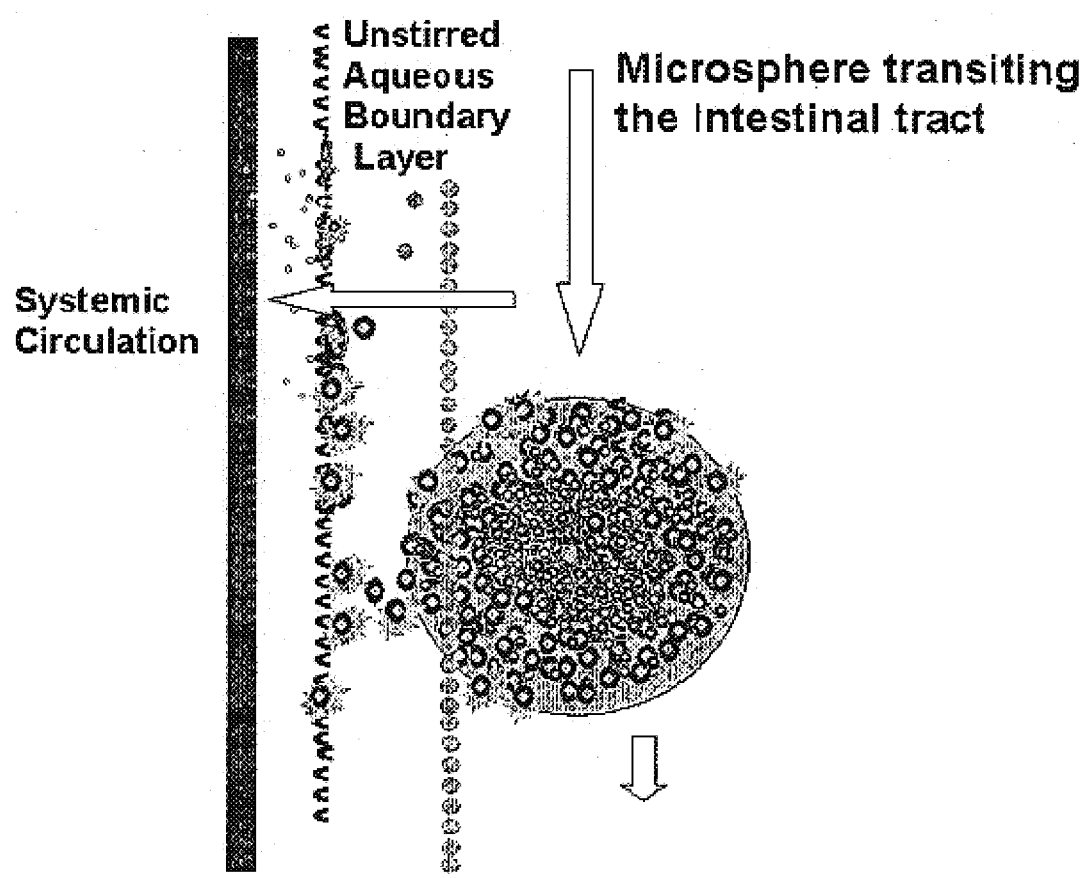
FIG. 10. is a graphical representation of the drug delivery mechanism hypothesized for the micro-spherical microcapsule matrices as they transit the intestinal tract, releasing the nifedipine particles in the form of protected gelled particles that adhere to the intestinal wall permitting prolonged release of nifedipine.

The present compositions designed to deliver bioactive compound to a subject in the small intestine are in one aspect preferred, in view of the relatively short onset time of such a system. In a typical healthy adult human subject, stomach contents are emptied within 30 minutes to one hour. Absorption in the duodenum may commence immediately thereafter and continue as the pharmaceutical composition transits the duodenum, jejunum and ileum. The transit time is approximately 3 hours. The present invention provides for the delivery of a microsphere having a surface that is substantially unaffected by the low pH environment in the stomach. For those compositions of the present invention that include a lipase-sensitive matrix material, the pancreatic lipases and bile salts secreted into the upper portion of the duodenum immediately work to dissolve and enzymatically degrade the lipase-sensitive matrix. As this degradation proceeds, the aqueous gastrointestinal milieu infiltrates into the developing crevices and pathways made in the microspheres. The hydrophilic shells coatings of the microcapsules found at the inner regions of the microspheres absorb the infiltrating water and swell, becoming solubilized and thereby participating in the rapidly eroding structure of the spheres. The swollen microcapsules slough off the eroding spheres and tend to adhere, along with emulsifying lipid materials, to the mucus layer adjacent to the membrane of the intestinal lumen. As the lipid material of the matrix continues to be digested, more and more of the microcapsules are released, and become admixed with the mucus layer. The relatively large surface area of the particles cores permit the rapid dissolution of the bioactive compound, which is held in close proximity to the intestinal membrane by the mucoadhesive swollen charged hydrophilic shell material. This process is depicted in FIG. 10.

Compositions of the present invention, having the capability to permit the small intestinal release mechanism, do so for a time substantially longer than the three-hour transit time observed for small intestine passage. The mucoadhesive nature of the charged hydrophilic materials increases the residence time of the sloughed-microcapsules deposited in the small intestine. The present compositions enable the delivery of bioactive compound in the small intestines for at least about 6 to about 24 hours, and in some cases longer, up to about 36 hours.

Compositions that Release in the Small and Large Intestine

Another embodiment of the present invention is designed to deliver bioactive compound to a subject in the small and large intestines, which is also preferred, in view of the combination of relatively prompt delivery and the relatively long duration of delivery in the large intestine. In a typical healthy adult human subject, small intestinal contents are passed to the cecum within about 3 hours after gastric emptying. Transit through the large intestine after ileum emptying can take anywhere from about 11 to about 36 hours. The present invention provides for the delivery of a microsphere having a surface that is substantially unaffected by the environment in the stomach, that is susceptible to partial degradation in the small intestine and that is susceptible to further enzymatic degradation in the large intestine. These compositions include preferably a matrix comprising two components, as described above. A first component is largely indigestible in the gastrointestinal tract, providing a superstructure or webbing to transport the microcapsules through the length of the intestinal tract. The second component dissolves or is degraded in the small intestine as a result of lipase degradation and/or bile surfactant-mediated dissolution. As this degradation proceeds, the aqueous gastrointestinal milieu infiltrates into the developing crevices and pathways made in the microspheres. The hydrophilic shells coatings of the microcapsules found at the inner region of the microspheres absorb the infiltrating water and swell, becoming solubilized and thereby participating in the more slowly eroding structure of the spheres. The swollen microcapsules slough off the eroding spheres and tend to adhere, along with emulsifying materials, such as lipids and fatty alcohols, to the mucus layer adjacent to the membrane of the intestinal lumen. As the materials of the matrix continue to be digested, more and more of the microcapsules are released, and become admixed with the mucus layer. The relatively large surface area of the particles cores permit the rapid dissolution of the bioactive compound, which is held in close proximity to the intestinal membrane by the mucoadhesive swollen charged hydrophilic shell material. The extant of the microcapsule deposition, or alternatively, diffusion through the swollen hydrophilic shell barrier, depends largely on the lipid-sensitive or alcohol content of the matrix. The microspheres or portions thereof that have not been depleted of microcapsules after the transit of the small intestine will empty into the cecum and be presented with an environment enriched in bacterial population. Continued delivery of the bioactive compound depends on the solubility rate of the particles in the large intestine. Compositions that are capable of releasing bioactive compound in the large intestine will continue to function.

The present compositions that are designed to continue drug delivery in the large intestine preferably incorporate hydrophilic charged polymers that are digestible by bacterial enzymes residing in the large intestine. As the bacterial enzymes continue to erode the water swollen hydrophilic shells of the microcapsules, the bioactive core particles are provided a means to solubilize and to transit the intestinal membrane.

The methods according to the present invention relate to administering a sustained-release pharmaceutical composition containing bioactive compound to a patient in need thereof, comprising administering to said subject a pharmaceutically effective amount of composition including the microspheres comprising the microcapsule matrices described hereinabove. A most preferred method provides for the administration of a composition wherein the bioactive compound is released to said patient from said composition over a period of time of from about 8 to about 36 hours, and preferably from about 8 to about 24 hours, and alternatively about 12 to about 30 hours, and most preferably from about 18 to about 24 hours.

The present method increases the solubility of bioactive compounds that are sparringly soluble to water insoluble. A further aspect of the present method increases the permeability of bioactive compounds that exhibit low permeability. A special embodiment of the present method increases the bioavailability of the bioactive compound by inhibiting metabolic degradation of said bioactive compound in the gastrointestinal tract.

An exemplary bioactive compound used as a model to demonstrate the present invention is nifedipine. Nifedipine is a dihydropyridine derivative, 1,4-Dihydro-2,6-dimethyl-4-(2-nitrophenyl)-3,5-pyridinedicarboxylic acid dimethyl ester, having the empirical formula $C_{17}H_{18}N_2O_6$, and the following structural formula.

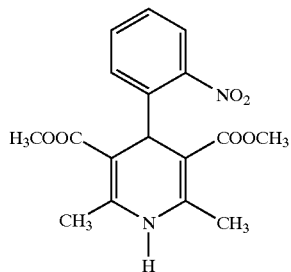

Nifedipine is a calcium ion influx inhibitor (calcium entry blocker or calcium ion antagonist) and blocks the transmembrane influx of calcium ions into muscle cells. In particular it blocks the influx of calcium through the slow channels without significantly affecting influx through fast channels. This action results in a reduction of intracellular calcium available for muscular contraction. This is particularly evident with vascular smooth muscle and less so with cardiac muscle[1,2]. The minimum effective concentration for humans is reported to be 15 ng/mL[1]. The usual daily dose of nifedipine is 30–90 mg for angina and 30–120 mg for hypertension[2].

[1]Therapeutic Drugs, Edited by Colin Dollery, Churchill Livingstone, 1999, Second Edition, Volume 1, p C244.
[2]Compendium of Pharmaceuticals and Specialities (CPS), 33rd edition, 1998, Login Brothers Canada, CD-ROM Database The absorption of nifedipine from the human gastrointestinal tract is reported to be over 90% but systemic bioavailability is only about 45–70%[1] probably as a result of extensive presystemic metabolism. Food has been shown to delay the time to peak concentrations when taken with conventional formulations but to increase the rate of absorption from slow/controlled release gastro-intestinal therapeutic system (GITS) formulations. However, the extent of absorption is not altered by food.

After absorption, nifedipine undergoes extensive metabolism in the liver via cytochrome P450 to three main metabolites but principally by oxidation to the pyridine (hydroxy-carboxylic acid) metabolite (70–95%) followed by hydrolysis. A lactone metabolite accounts for most of the remaining metabolism. These metabolites are thought to be devoid of any pharmacological activity. Nifedipine is widely distributed into body tissues with a steady state volume of distribution of 0.3–1.2 $l.kg^{-1}$ and pharmacokinetic profiles suggest a rapid distribution phase and slower terminal elimination phase.

Nifedipine is insoluble in water and is reported to have only about 50% bioavailability in rats. An early experimental observation demonstrates that the present composition and method increases the bioavailability of nifedipine in the rat model to close to 100%. Applicants believe that the mechanisms underlying the absorption enhancement of nifedipine in the rat are more than likely to apply to the enhancement of the bioabsorption and bioavailability enhancement of many other bioactive compounds in rats as well as other animals, including humans.

Small molecule drugs that exhibit limited bioavailability in humans and that are capable of being formulated into a higher bioavailable composition and used in the present method to provide a higher availability administration include, but are not limited to, felodipine, nimodipine, verapamil, the nonsedating antihistamines, including terfenadine, astemizole, the benzodiazepines, alprazolam, triazolam, midazolam, the cholesterol lowering drugs, lovastatin, simvastatin, atorvastatin, immunosuppressive agents, such as cyclosporine, tacrolimus, and alfentanil, codeine; fentanyl, methadone, clarithromycin, erythromycin, azithromycin, paclitaxel, tamoxifen, vincristine, astemizole, chlorpheniramine, montelukast, salmeterol, amiodarone, quinidine, carvedilol, losartan, propranolol, amlodipine, diltiazem, lercanidipine, nicardipine, nisoldipine, nitrendipine, verapamil, cerivastatin, simvastatin, pravastatin, fluvastatin, cisapride, indinavir, nelfinavir, ritonavir, saquinavir, estradiol, estrogens, progesterone, progestins, testosterone, hydrocortisone, alprazolam, diazepam, midazolam, triazolam, zaleplon, zolpidem, buspirone, haloperidol, pimozide, quetiapine, carbamazepine, cilostazol, dapsone, dextromethorphan, donepezil, finasteride, lidocaine, odanestron, quinine, sildenafil, tamsulosin, and trazodone.

Peptide active ingredients that may benefit from oral delivery in accordance with the invention include any therapeutic agent that is physiologically active and has a plurality of amino acids and at least one peptide bond in its molecular structure. The present compositions enhance the ability of peptide and proteins to transit the intestinal membrane if formulated to delay most bioactive release until reaching the large intestine where membrane peptidases are less abundant. Further, the invention, by several mechanisms, is believed to suppress the degradation of the active ingredients by protease that would otherwise tend to cleave one or more of the peptide bonds of the active ingredient. The molecular structure may further include other substituents or modifications. For example, salmon calcitonin, a preferred peptide active agent herein, is amidated at its C-terminus. Both man-made and natural peptides can be orally delivered in accordance with the invention.

Peptide active compounds useful in the present invention include, but are not limited to, naturally derived and recombinantly produced proteins and peptides such as insulin, vasopressin, calcitonin (including not only the preferred salmon calcitonin, but other calcitonins as well). Other examples include calcitonin gene-related peptide, parathyroid hormone, luteinizing hormone-releasing factor, erythropoietin, tissue plasminogen activators, human growth hormone, adrenocorticotropin, various interleukins, enkephalin, Factors VIII, IX and X, and the like. Many others are known in the art. It is expected that any pharmaceutical compound having peptide bonds which would be subject to proteolysis in the gastrointestinal tract would benefit from oral delivery in accordance with the present invention because of the reduction in such proteolysis, and protection therefrom, that is afforded by the present invention.

The compositions of the present invention comprises a pharmaceutically effective amount of the bioactive compound, that is, an amount that is effective in achieving the desired prophylactic, therapeutic or diagnostic effect in the patient. It should be appreciated that the amount of bioactive compound comprising the composition will depend on various factors, including, for example, the particular bioactive compound used, the nature of the condition to be treated, and the nature of the patient. Similarly, the hydrophilic polymer and/or the aliphatic alcohol contained in the composition of the present invention are present in an amount that is effective in increasing the bioavailability and/or absorption properties of the bioactive compound. The amount of polymer and/or the aliphatic alcohol in the composition will depend on various factors, including, for example, the particular bioactive compound(s) used, the amount of bioactive compound(s), the particular polymer and/or the aliphatic alcohol used, the optical isomeric form of the bioactive compound, that is racemic or optically pure.

The compositions of the present invention comprise optionally a vehicle, the nature of which will depend on the form of the composition. The microspheres of the present composition can be used in any suitable form, for example, compressed in the form of a tablet, in the form of multiparticulates filled in a capsule and suspended in a liquid carrier. Aside from the sustain release properties of the composition of the present invention, the tablets and capsules can be further modified to provide additional delayed release, sustained release, or immediate release characteristics. It is believed that the composition of the present invention will be used most widely in solid oral dosage form.

The term "vehicle" is used broadly to include various types of pharmaceutically acceptable ingredients that can comprise the composition other than the bioactive compound and polymer and/or the aliphatic alcohol constituents of the composition. Examples of vehicles include fillers, diluents, excipients and materials, which have an effect on the release properties of the bioactive compound, that is, control-release materials.

Fillers or bulking agents include, but are not limited to, microcrystalline cellulose (e.g., Avicel.RTM., FMC Corp., Emcocel.RTM., Mendell Inc.), mannitol, xylitol, dicalcium phosphate (e.g. Emcompress, Mendell Inc.) calcium sulfate (e.g. Compactrol, Mendell Inc.) starches, lactose, sucrose (Dipac, Amstar, and Nutab, Ingredient Technology), dextrose (Emdex, Mendell, Inc.), sorbitol, cellulose powder (Elcema, Degussa, and Solka Floc, Mendell, Inc.) The bulking agent may be present in the composition in an amount of from about 5 wt. % to about 90 wt. %, preferably from about 10 wt. % to about 50 wt. %.

Disintegrating agents that may be included in the composition include, but are not limited to, microcrystalline cellulose, starches, crospovidone (e.g. Polyplasdone XL, International Specialty Products.), sodium starch glycolate (Explotab, Mendell Inc.), and crosscarmellose sodium (e.g., Ac—Di—Sol, FMC Corp.). The disintegrating agent may be present in the composition in an amount of from about 0.5 wt. % to about 30 wt %, preferably from about 1 wt. % to about 15 wt. %.

Antiadherants and glidants which may be employed in the composition include, but are not limited to, talc, corn starch, silicon dioxide, sodium lauryl sulfate, and metallic stearates. The antiadherant or glidant may be present in the composition in an amount of from about 0.2 wt. % to about 15 wt. %, preferably from about 0.5 wt. % to about 5 wt. %.

Lubricants which may be employed in the composition include, but are not limited to, magnesium stearate, calcium stearate, sodium stearate, stearic acid, sodium stearyl fumarate, hydrogenated cotton seed oil (sterotex), talc, and waxes, including but not limited to, beeswax, carnauba wax, cetyl alcohol, glyceryl stearate, glyceryl palmitate, glyceryl behenate, hydrogenated vegetable oils, and stearyl alcohol. The lubricant may be present in an amount of from about 0.2 wt. % to about 20 wt. %, preferably from about 0.5 wt. % to about 5 wt. %.

Binding agents which may be employed include, but are not limited to, polyvinyl pyrrollidone, starch, methylcellulose, hydroxypropyl methylcellulose, carboxymethyl cellulose, sucrose solution, dextrose solution, acacia, tragacanth and locust bean gum. The binding agent may be present in the composition in an amount of from about 0.2 wt. % to about 10 wt. %, preferably from about 0.5 wt. % to about 5 wt %.

The compositions of the present invention may be made by a direct compression method, or by a wet granulation method. In the direct compression method, the microspheres and other ingredients are sieved through a stainless steel screen, such as a 40 mesh steel screen. The sieved materials then are charged to a suitable blender, and blended for 10 minutes with an intensifier bar on for 3 minutes. The blend then is compressed into tablets on a rotary press using appropriate tooling. The compressed tablets may be coated, if desired.

In the wet granulation method, the microspheres and other ingredients are granulated with a granulating fluid (e.g., isopropyl alcohol, ethyl alcohol, and water) in a planetary mixer, high shear mixer, or fluidized bed granulator. Binding agents may be contained in the granulating fluid, or may be in the dry mix. The wet granules are dried in an oven or fluidized bed dryer, and then sieved through a suitable screen to obtain free flowing granules. The resulting granules were blended with a suitable lubricant and glidant, and the lubricated granules are compressed into tablets on a rotary press using appropriate tooling. If desired, a coating can be applied onto the compressed tablets.

The present invention also relates to the process for the manufacture of the present microspheres. The process comprises spraying, into a chilling zone the temperature below the solidification temperature of the water insoluble fluid matrix material, a flowable dispersion of bioactive micronsized organic particles containing charged organic moieties in a water insoluble fluid matrix, under conditions that form droplets of said dispersion. The process preferably maintains the fluidity of the droplets for a time sufficient to distribute the particles homogenously within the droplets, prior to the solidification of the droplets into microspheres. It is believed that during the spraying process that the bioactive charged particles are drawn to the interior of and are drawn from the surface of the droplets while fluid.

The temperature of the fluid mixture as reaches the spray nozzle should be maintained below the melting temperature of said matrix material but above its solidification temperature. The temperature of the spraying, the configuration of the spray nozzle, and the flow rate through the nozzle all influence the physical characteristics of the resulting microspheres. A most preferred process uses a heated spray nozzle (and heated tubings and conduits leading up to said nozzle) that ensures that the pressure-treated mixture maintains a viscosity suitable for a high spray throughput. Such high throughput enables the formation of substantially spherical microspheres upon cooling the sprayed particles of liquid mixture below the solidification temperature of the matrix material.

The flowable matrix material most preferably exhibits a melting curve where melting begins at T1 and is substantially complete at T2, and exhibits a cooling curve where solidification begins at T3 and is substantially complete at T4, wherein T3 is less than T1. The difference between T1 and T2 for any particular matrix material used in the present method is determined by the ratio of materials comprising said flowable medium matrix. By modifying the ratio of components, the temperature characteristics, and hence temperature-dependent release characteristics, of the microspheres produced by the present method, may be modified. Furthermore, by determining the melting and solidification temperatures for the particular matrix material used in the present method, the temperatures of the mixture during treatment may be adjusted accordingly to avoid jamming or clogging of the apparatus during operation.

The preferred process utilizes a water insoluble organic matrix material that melts between about 120 degrees F. and about 225 degrees F., and the process maintains the flowable dispersion at a temperature above the solidification temperature of said water insoluble medium, but below the melting temperature of said water insoluble medium. A more preferred process employs a water insoluble matrix having a melting point that starts at about 106 degrees F. and is substantially complete at about 140 degrees F.

A preferred process sprays the flowable mixture under pressure. An alternative process sprays through an electrically charged spray nozzle.

The suspended particles in the flowable mixture are preferably bioactive particles containing a charge, or at least sufficient dipole moment to become oriented in an electric field of the strengths generated by the spraying operation. A most preferred bioactive sub-micron organic particles containing charged organic moieties are the microcapsules having a coating or shell consisting essentially of the charged hydrophilic materials described hereinabove. The shell material may have water associated with it in amounts that do not inhibit the encapsulation of the bioactive core during high pressure processing as described herein below. Embodiments of such materials include pharmaceutically acceptable, water soluble polyanionic polymers, and in particular those polymers that consist essentially of a polymeric backbone to which a plurality of pharmaceutically acceptable alkyl carboxylic acid addition salts or alkyl phosphate acid addition salts are covalently bonded, and most particularly a polymer backbone selected from the group consisting of cellulose, hemicellulose, galactose polymer and 3,6-anhydro-galactose copolymers. The shell may be cross-linked, preferably with a multivalent cation, such as calcium, magnesium or Fe+3.

A further aspect of the present process contacts the solidified microspheres with a static discharge composition comprising a dilute aqueous solution of antistatic agent. The contacting may be either immersion or spray misting. Spray misting is preferred.

The flowable medium used to conduct the spraying operation is preferably obtained by first subjecting a dispersion of bioactive organic particles and a water soluble organic material containing charged organic moieties in a water insoluble fluid medium to sufficient high-pressure forces to form said flowable dispersion of bioactive sub-micron organic particles. This process is applied to said dispersion of bioactive organic particles having a mean particle diameter size of greater than one micron. The forces applied involve compression, shear and cavitation forces. A most preferred means of applying these forces is to apply high pressure to the flowable composition for less than a second at a pressure of from about 2,000 psi to about 20,000 psi. A particular embodiment of this pressure application passes the compressed mixture through a chamber that subjects said mixture to cavitation and/or shear forces.

A particularly preferred aspect of the process invention is the modification of the bioactive micronized organic particles that comprise a polyanionic polymer shell material. This method contacts the flowable dispersion containing these polymeric capsules with a micronized or sub-micron water-in-oil emulsion of an aqueous solution of a multivalent cation in said water insoluble fluid medium. The cation may be any multivalent cation useful for cross-linking polyanionic polymers, such as calcium, magnesium or iron +3. The amount of sub-micron emulsion used is only that amount sufficient to "wet" substantially all of the capsules in the flowable dispersion, thereby effecting a superficial cross-linking of the capsules while minimizing swelling of the polymeric shells. Preferred molar amounts range from a ration of about 0.001 to about 0.5 moles of divalent cation per mole of anionic group present in the flowable dispersion. A more preferred range is from about 0.01 to about 0.2 moles of cation per mole of anionic group. The addition of the cation results in the formation of a flowable dispersion of bioactive organic particles encapsulated with a cross-linked moisture-containing polyanionic polymer.

The sub-micron emulsion is dispersed in the flowable dispersion by adding the emulsion to the dispersion. The emulsion is preferably not highly concentrated, and most preferably in a concentration that when added to the flowable dispersion disperses easily therein. The mixture is carried out preferably by slowly dispersing the emulsion in the flowable dispersion. The rate of addition depends on the concentrations of particles in the emulsion and dispersions, as well as the rate of stirring. The use of low shear homogenization equipment is preferred. This method will permit the individual wetting of the capsules with the aqueous sub-micron droplets of the emulsion. As the individual capsules are wetted the polymer chains on the surfaces of the contacted capsules cross-link and strengthen their structural integrity. By minimizing the amount of water in the submicron emulsion, the multivalent cation may be added with minimal swelling of the capsules.

The emulsions used in the present invention may comprise additional materials, such as water-soluble bioenhancers, and anti-oxidants. A preferred aspect of these emulsions is that the additional material may comprise the salt of the multivalent cation described above. Most preferred materials include calcium ascorbate and calcium citrate.

Further processing of the formed microspheres may include contact with a second amount of water insoluble material soluble at pH greater than about 6. A preferred means of accomplishing this contacting is with spray coating. The pH>6 material applied may comprise from about 5 to about 30 percent by weight of said water insoluble matrix material used to form said solidified microsphere, and preferably the pH>6 material is about 10 percent by weight of said second amount of said water insoluble matrix material. Such material may be selected from the group consisting of triglycerides, hydrogenated vegetable oils, and mono-, di and tri-glyceride esters and ethers of polyalkoxyalkyl alcohols.

A particularly preferred process further comprises annealing said solidified composition. Annealing may comprise heating the solidified composition to a temperature less than the melting point of the water insoluble organic material for a period of time ranging from about one minute to about four hours. The annealing time is variable depending on the particular organic material used. Annealing is particularly preferred when said water insoluble material is capable of solidifying into more than one crystalline form, such as a polymorphic material, for example, when said polymorphic material comprises a triglyceride wax.

The pressure force is applied to the pre-mixture in accordance with the method and apparatus (Beta apparatus) described in U.S. Pat. No. 5,209,879, which is hereby incorporated by reference. The compressive forces are generated by compacting the pre-mixture during a short time interval and forcing the compacted pre-mixture through the "beta" chamber thereby subjecting the mixture to a shear and cavitation forces resulting from the high-pressure surges and currents created in a post pressure reduction chamber. This process is described in U.S. Pat. Nos. 4,978,483, 5,460,756, and 5,209,879 all hereby incorporated by reference. The amount of pressure force required, in the present invention, depends on the time interval during which the pressure is applied. The required pressure varies inversely with that time interval. The pressure pulse process continues as long as the pressure is maintained on the pre-mixture, but the matrix dispersion is most effective when the pressure is applied for a very short period of time, preferably on the order of one second or less. To amplify the effectiveness of the pressure force processing, the pressure-treated mixture may be repeatedly subjected to the application of pressure in the Beta apparatus. The flowable composition may be passed through the Beta apparatus one, two or even three times to achieve the desired effect size reduction and encapsulation The core material may be the untreated bioactive compound in the form of a solid, liquid, or slurry, or the bioactive compound in the form of the aforesaid capsules, in the form of a solid, or slurry. As a result of the application of the high-pressure forces, the particles collide, fracture and generally become reduced in size. After two to five passes through the high-pressure device, the mean particle size is less than about five microns, but a significant amount of particles on the order of about one micron or less as well as particles of larger size on the order of 5–20 microns are still observable. Furthermore the hydrophilic charged material surface coats or encapsulates the reduced size particles, or forms an imbedding media for one or more particles of active, resulting in the microcapsules of the present invention.

The release properties of the microspheres prepared using the aforesaid two-step process is a function of the percentage of microcapsules in the microsphere matrix composition, the relative amount of ionic salt groups in the charged polymer encapsulating the bioactive compound in the microcapsules, the size and shape of the microspheres, and the composition of the encapsulating shell and matrix material.

The sustained release rate is believed to occur due to the erosion of minute imperfections in the microspheres of the present invention which form "tortuous" paths throughout the matrix of the inner encapsulate thereby providing ingress of aqueous media and egress of solubilized capsules.

Depending on the environmental conditions to which the present microspheres are subjected, the minor cracks or fissures may widen and accelerate core release. The present microspheres are capable of being designed to respond to such conditions to achieve a desired release effect. For example, the matrix material composition may be designed to melt between a specified temperature range, thereby releasing the core material suddenly or over a period of seconds, to minutes to an hour or more. The capsule is capable of being designed to release its core slowly at or about human or animal body temperature, or as a function of ambient temperature, for example on days where the air temperature rises above a set point such as 100 degrees F. Such temperature sensitive microspheres are useful in the formulation of compositions for rectal, buccal and dermal applications.

The following examples illustrate the present invention and show the unexpected properties achieved by the present invention in comparison to compositions not comprising the present invention.

EXAMPLES

Control Example A

Microspheres of Particulate Nifedipine in a Matrix Consisting of Polymorphic Wax 525 g of milled nifedipine (<10 micron particle size) is mixed into a melt of 975 g of Sterotex NF C, a commercially available polymorphic wax at a temperature of 79.6 degrees C. with stirring. The flowable pre-mixture is then subjected to a pressure-force by passing it three times through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through a Nordson hot melt applicator maintained at about 180 degrees F., driven by an electronic gear pump (Nordson 3700 series, speed setting= 30%), aspirator pressure of 15 psi, needle set at ⅞ of a turn open from closed, into a chilled area. The nifedipine comprises about 30% by weight of the capsule composition. All work is done in a red light environment.

The capsule prepared according to Control Example A is capable of a sustained release of its core nifedipine and exhibits a zero order release profile when administered orally to a rat.

Control Example B
Microspheres of Particulate Nifedipine in a Matrix Consisting of Cetyl Alcohol 525 g of milled nifedipine (<10 micron particle size) is mixed into a melt of 975 g of cetyl alcohol, NF, (CO-1695F Procter & Gamble) at a temperature between about 55 and 62 degrees C. with stirring. The flowable pre-mixture is heated to about 70 degrees C. then subjected to a pressure-force by passing it three times through a hydraulic piston driven pump, the "Beta" machine described in U.S. Pat. No. 5,209,879, set at 90 psi (Beta chamber configuration= entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through a Nordson hot melt applicator maintained at about 170 degrees F., driven by an electronic gear pump (Nordson 3000 series, speed setting=30%), aspirator pressure of 15 psi, needle set at ⅞ of a turn open from closed, into a chilled area. The nifedipine comprises about 35% by weight of the capsule composition. All work is done in a red light environment.

The capsule prepared according to Control Example B is capable of a sustained release of its core nifedipine and exhibits an accelerated sustained release profile when administered orally to a rat.

Control Example C
Microspheres of Particulate Nifedipine in a Matrix Consisting of a Polymorphic Wax and Cetyl Alcohol 538.5 g of milled nifedipine (<10 micron particle size) is mixed into a melt of 500 g of cetyl alcohol, NF, (CO-1695F Procter & Gamble) and 500 g of Sterotex NF C, a commercially available polymorphic wax at a temperature between about 73 and 78 degrees C. with stirring. The flowable pre-mixture is equilibrated at about 72 degrees C. and then subjected to a pressure-force by passing it three times through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through a Nordson hot melt applicator maintained at about 170 degrees F., driven by an electronic gear pump (Nordson 3000 series, speed setting=30%), aspirator pressure of 15 psi, needle set at ⅞ of a turn open from closed, into a chilled area. The nifedipine comprises about 35% by weight of the capsule composition. All work is done in a red light environment.

The capsule prepared according to Control Example C is capable of a sustained release of its core nifedipine and exhibits an accelerated sustained release profile when administered orally to a rat.

Example 1A
Nifedipine Capsule Pretreatment 195 g of milled nifedipine (<10 micron) is dispersed completely in a aqueous solution of sodium carboxymethylcellulose (97.5 g) (in 2.7 liters of distilled water) using a high speed homogenizer (Silverson homogenizer, Model No. L4RT at 8000 rpm). After addition, stirring is continued for about 10 min at 9500 rpm. The dispersion is stored in a container protected from exposure to light. The homogenized mixture is then spray dried (Bowen Industries Co., spray dryer—30 inch diameter lab unit, 0.125 mm diameter nozzle from Spray Systems Inc.) at 300° F. inlet and 213° F. outlet, using 60 psi air pressure and a feed rate of 60 ml/min. (peristaltic pump) resulting in fine particles of nifedipine/CMC material.

Example 1B
Microspheres of Nifedipine Microcapsules in a Matrix Consisting of Polymorphic Wax 525 g of CMC-treated nifedipine (nifedipine milled to <10 micron particle size spray dried with sodium carboxymethylcellulose according to Example 1 above) is mixed into a melt of 975 g of Sterotex NF C, a commercially available polymorphic wax at a temperature of about 78 degrees C. with stirring. The flowable pre-mixture is then subjected to a pressure-force by passing it three times through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacer with a length of about 0.04 in and a diameter of about 0.25 in, a baffle plate consisting of 4 holes (0.02 in ID), a second spacer, and an exit nozzle consisting of four holes (0.02 in ID)). The pressure-treated mixture is sprayed through a Nordson hot melt applicator maintained at about 174 to 179 degrees F., driven by an electronic gear pump (Nordson 3700 series, speed setting=30%), aspirator pressure of 15 psi, needle set at ⅞ of a turn open from closed, into a chilled area. All work is done in a red light environment.

Example 2
Microspheres of Nifedipine Microcapsules in a Matrix Consisting of Polymorphic Wax and Cetyl Alcohol 500 g of nifedipine microcapsules (66% nifedipine milled to <10 micron particle size encapsulated in sodium carboxymethylcellulose according to Example 1 above) is mixed into a melt of 487.5 g of cetyl alcohol, NF, (CO-1695F Procter & Gamble) and 487.5 g of Sterotex NF C, a commercially available polymorphic wax at a temperature between about 75 and 80 degrees C. with stirring. The flowable pre-mixture is equilibrated at about 72 degrees C. and then subjected to a pressure-force by passing it three times through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacer with a length of about 0.04 in and a diameter of about 0.25 in, a baffle plate consisting of 4 holes (0.02 in ID), a second spacer, and an exit nozzle consisting of four holes (0.02 in ID). The pressure-treated mixture is sprayed through a Nordson hot melt applicator maintained at about 179 degrees F., driven by an electronic gear pump (Nordson 3000 series, speed setting=30%), aspirator pressure of 15 psi, needle set at ⅞ of a turn open from closed, into a chilled area. The nifedipine microcapsules comprise about 35% by weight of the microcapsule composition. All work is done in a red light environment.

In Vivo Studies of Pharmacokinetic Profiles of Formulations of Examples A, B and C and Examples 1 and 2

This study determines the pharmacokinetic profiles of sustained release (SR) oral formulations of nifedipine in male rats in comparison to an immediate release (IR) oral solution and an intravenous dose.

Thirty-nine male Sprague-Dawley rats (Ace Animals, Inc.) are divided into 7 groups of 3 rats/group. Each group is dosed with one of 5 sustained release (SR) formulations, the immediate release (IR) formulation or the intravenous (IV) formulation described in the following Table 1:

TABLE 1

| Group Number | Formulation (Example No.) | Microsphere Description | Route | Targeted Dose (mg/kg)[a] |
|---|---|---|---|---|
| 1 | Control Example A | Excipient: None<br>Shell material: Sterotex | Oral | 3.6 |
| 2 | Control Example B | Excipient: None<br>Shell material: Cetyl alcohol | Oral | 3.6 |
| 3 | Control Example C | Excipient: None<br>Shell material: Cetyl alcohol/Sterotex | Oral | 3.6 |
| 4 | Example 1 | Excipient: CMC<br>Shell material: Sterotex | Oral | 3.6 |
| 5 | Example 2 | Excipient: CMC<br>Shell material: Cetyl alcohol/Sterotex | Oral | 3.6 |
| 6 | Solution (IR) | | Oral | 3.6 |
| 7 | Solution | | Intravenous | 0.1 |

[a] Based upon a 250 g rat

The SR formulations are prepared in according with Control Examples A, B and C and Examples 1 and 2. The nifedipine load for each microsphere formulation is determined by HPLC and the appropriate weight of microspheres to deliver a dose of 3.6 mg/kg to a 250 g rat is placed in an opaque gelatin capsule. For dosing, the contents of the capsule are emptied into the hub of a gavage needle. A syringe filled with 3 ml of water is attached to the gavage needle and the microspheres are flushed into the stomach.

The IR (0.5 mg nifedipine/ml in a 30% sodium benzoate solution) and intravenous (0.05 mg nifedipine/ml in a 30% sodium benzoate solution) dose solutions are prepared using the same lot of nifedipine used to make the sustained release formulations. Nifedipine concentrations in the dose solutions are verified by UV absorbance. The IR dose solution (1.8 ml) is administered via oral gavage. For intravenous administration, each rat is restrained and 0.5 ml of the dose solution is slowly infused over 4 minutes by hand via the lateral tail vein.

Since nifedipine is highly photosensitive, all necessary precautions are taken during the preparation, storage and dosing of the formulations to protect them from exposure to natural and artificial light. Rats are not fasted prior to dose administration.

Blood/Plasma Collection

Blood samples (~0.25 ml) are collected by jugular vein puncture. For the oral doses, blood samples are collected predose and then at 0.25, 0.5, 1, 2, 4, 6, 8 and 10 hours following dose administration. For the intravenous dose, blood samples are collected predose, at the end of the infusion and then at 0.25, 0.5, 0.75, 1, 1.5, 2, 3 and 4 hours following the end of the infusion. The blood samples are transferred into polypropylene tubes (covered with aluminum foil and containing lithium heparin as anticoagulant). Plasma samples are separated using a refrigerated centrifuge and stored frozen at −65° C. in foil covered polypropylene tubes.

Plasma Analysis

The analytical method used to measure nifedipine is based on a previous method developed for nifedipine in human heparinized plasma. A 2-day re-validation is performed in the rat plasma matrix. Standards and controls are prepared in heparinized rat plasma. All samples underwent liquid-liquid extraction to isolate nifedipine, followed by reversed phase chromatography, and quantitative detection using MRM mass spectrometry. The internal standard used is a d-6 stable isotope of nifedipine.

The analytical range of the method is 5.00 ng/ml to 500 ng/ml using a 50 ul sample. Precision (CV) and accuracy (difference) of quality controls across the range are consistently below 15% during the 2 validation runs. Studies of the stability of nifedipine in plasma samples for 4 hours at room temperature, and through 3 freeze-thaw cycles indicated no loss of nifedipine.

Data Analysis

For each pharmacokinetic profile, the highest observable concentration is assumed to be the maximum concentration (Cmax). The time that Cmax is reached is denoted Tmax. Area under the plasma concentration-time curve (AUC) is calculated from zero to the last quantifiable plasma concentration, AUC(tf), using the linear trapezoidal rule. For intravenous administration, the terminal half-life is calculated from the relationship ln $2/K_{el}$. Kel is defined as the slope of the terminal monoexponential phase of the concentration-time profile and is calculated by log-linear regression of the data. AUC from zero to infinity (AUCinf) is calculated as the sum of AUC(tf) plus the ratio of the plasma concentration at tf to Kel. Since both the nifedipine plasma-concentration data from the different oral formulations and, in general, individual rats dosed with the same formulation are highly variable, the approximate time that nifedipine concentrations are greater than one half Cmax is used as a measure to normalize the data and define the release profile. Meier J, Neüsch E, Schmidt R. Pharmacokinetic criteria for the evaluation of retard formulations. Eur J Clin Pharmacol 1974; 7:429–432.

Results

All animals are dosed successfully. For the microsphere formulations, one rat receiving the composition of Example 4 required an additional 1 to 4 ml of water to completely flush the entire dose into the stomach. The extensive bleeding procedure did result in some stress to the animals and one animal receiving the composition of Control Example A, Example C and the IR composition died before all the scheduled blood samples could be drawn.

Individual concentrations of nifedipine in plasma for the 7 formulations evaluated are reported in Tables 1–7 and graphically presented in FIGS. 1–7. All analytical data met the acceptance criteria for the assay. Plasma concentrations that are below the quantifiable limit of 5 ng/ml are reported as zero.

Following intravenous administration of nifedipine, maximum plasma concentrations are observed at the end of the 4-minute infusion. Plasma nifedipine concentrations then declined rapidly and are not detectable 1.5 hours post infusion. The terminal half-life is estimated at ~15 minutes which is in close agreement with that reported in the literature following a 6 mg/kg intravenous dose to rats. The data are summarized in the following Table 2.

TABLE 2

| Rat Number | Cmax (ng/ml) | AUCinf (ng · hr/ml) | t1/2 (min) |
|---|---|---|---|
| 2137 | 230 | a | a |
| 2138 | 223 | 64.1 | 16 |
| 2139 | 255 | 81.4 | 15 |

Note: Dose is 0.1 mg/kg
a: Animal died; parameter could not be estimated

Following oral administration of nifedipine in solution (IR formulation), nifedipine is rapidly absorbed and Cmax is observed at the first sampling time post dose (15 minutes). Plasma nifedipine concentrations steadily declined out to 2 hours and then showed some fluctuation over the next 8 hours (Table 3). Once Tmax occurred, plasma nifedipine concentrations are not maintained beyond this time which is in agreement with published data. Grundy J S, Eliot L A, Foster R T. Extrahepatic first-pass metabolism of nifedipine in the rat. Biopharm Drug Disp 1997; 18:509–522.Eliot L A, Foster R T, Jamali F. Effects of hyperlipidemia of nifedipine in the rat. Pharm Res 1999; 16:309–313. An oral bioavailability of ~50% for nifedipine in the rat has been reported, so a greater Cmax would have been expected in the current study from the IR formulation considering that a dose of 3.6 mg/kg is administered. The reason for the lower Cmax is unknown; the only difference is that 30% sodium benzoate, instead of polyethylene glycol 400, is used to solubilize nifedipine.

Compared to the IR formulation, there is a slower rate of absorption of nifedipine from all of the microsphere formulations with Cmax generally being achieved 2–4 hours post dose. In addition, the duration that plasma nifedipine concentration exceed greater than half Cmax generally ranged from 2 to 4 hours. There are, however, some marked differences in the extent of absorption of the nifedipine load between the different microsphere formulations that resulted in some formulations having greater Cmax and associated AUC values than others. Although the intravenous dose is 36-times less than the oral doses, it would appear, assuming linear pharmacokinetics, that the bioavailability of nifedipine (based upon AUC ratios) from the microsphere formulations of Example 4 and 5 would be about 100%. Although this would not have been expected, it is possible that it resulted from experimental variability and that the actual bioavailability was slightly lower. The data are summarized in the following Table 3:

TABLE 3

| | Parameter Range | | | | |
|---|---|---|---|---|---|
| Formulation | Cmax (ng/mL) | Tmax (hr) | tf[a] (hr) | AUC(tf) (ng · hr/mL) | Duration[b] (hr) |
| Control Example A | 80.8–120 | 4–6 | 10 | 508–680 | 6 |
| Control Example B | 188–469 | 2–6 | 10 | 1068–1767 | 2–4 |
| Control Example C | 260–406 | 4 | 10 | 1352–1745 | 2–4 |
| Example 1 | 307–864 | 1–4 | 10 | 1980–2736 | 1–4 |
| Example 2 | 471–611[c] | 2–6 | 10 | 2390–2917[c] | 3–5 |
| IR | 89.6–149 | 0.25 | 10 | 324–378 | 0.25 |

[a]Time of last quantifiable plasma concentration
[b]Time plasma concentrations are greater than half Cmax
[c]Normalized to a targeted dose of 3.6 mg/kg Compared to the immediate release oral solution, the window that plasma nifedipine concentrations remained above 50% of Cmax appeared to be longer for all of the microsphere formulations evaluated. The formulations that incorporated CMC as an excipient and/or included cetyl alcohol in their shell appeared to enhance the extent of absorption of nifedipine from the gastrointestinal tract. Those that incorporated CMC and cetyl alcohol obtained the maximum enhancement effect.

A second rat study was performed with six rats in each group. The formulations tested included the formulations used in the first study as well as formulations containing Sterotex as the matrix material and varying amounts of cetyl alcohol. The cetyl alcohol included in the matrix ranged from 2, 5, 10, 20, 50 and 100 wt percent based on the amount of total matrix material, with the balance of matrix material being Sterotex. The data from this second study is presented in Table 4 below.

TABLE 4

Second Study of Pharmacokinetics of Nifedipine in the Rat

| | Parameter Mean ± SD (Range) [N = 5 or 6] | | | |
|---|---|---|---|---|
| Formulations | Cmax (ng/mL) | Tmax (hr) | tf[a] (hr) | AUC(tf) (ng · hr/mL) |
| Control Example A 100% Sterotex | 25.0 ± 6.3 (17.4–34.2) | 3.6 ± 0.9 (2–4) | N/A (8–12) | 129 ± 46 (84.1–195) |
| Control Example B 100% Cetyl Alcohol | 170 ± 75 (34.0–248) | 3.2 ± 1.3 (1–4) | N/A (6–12) | 612 ± 285 (141–853) |
| Control Example C 50% Cetyl Alcohol | 119 ± 21 (99.8–148) | 2.7 ± 1.0 (2–4) | N/A (8–12) | 536 ± 79 (432–628) |
| Example 1 100% Sterotex | 674 ± 281 (402–1030) | 1.4 ± 0.5 (1–2) | N/A (10–12) | 1847 ± 542 (1356–2676) |
| Example 2 50% Cetyl alcohol | 449 ± 125 (216–588) | 2.7 ± 2.0 (1–6) | N/A (8–12) | 2093 ± 526 (1288–2693) |
| Control Example D Alcohol | 37.0 ± 8.1 (26.6–49.6) | 4.0 ± 1.3 (2–6) | N/A (6–12) | 188 ± 75 (132–320) |
| Control Example E 5% Cetyl Alcohol | 38.3 ± 7.3 (28.3–46.3) | 4.8 ± 2.7 (2–8) | N/A (8–12) | 209 ± 29 (167–248) |
| Control Example F 10% Cetyl Alcohol | 56.1 ± 7.8 (44.1–66.9) | 2.8 ± 2.6 (1–8) | N/A (8–12) | 280 ± 33 (235–323) |
| Control Example G 20% Cetyl Alcohol | 83.8 ± 41.9 (31.0–124) | 3.2 ± 1.8 (2–6) | N/A (6–12) | 314 ± 145 (99.2–468) |
| IR | 77.9 ± 19.0 (55.7–97.6) | 0.25 | N/A (8–10)[b] | 238 ± 95 (103–374) |

N/A: Not applicable
[a]Time of last quantifiable plasma concentration
[b]Last collection time point for IR administration was 10 hours post dose The second rat study confirmed the high bioavailability achieved with the formulations of Example 1 and 2. In addition, an approximately linear relationship between cetyl alcohol makeup for the microsphere matrix and the absorption of nifedipine was observed. The plasma level data was deconvulated based on a mean half-life of nifedipine in the rat of 15 minutes. The plasma level data and the linear uptake data is graphically presented in FIGS. 6 and 7 respectively. All formulations achieved a near linear delivery of nifedipine from about 0 to about 6 hours. The Formulations including the anionic polymer, Na CMC showed the highest bioavailability, and an extended release effect.

The formulation of Example 2, and four other formulations differing in the percentage of nifedipine in the microspheres were prepared and tested in a human clinical trial.
Human Clinical Study Twenty subjects are fasted for at least 10 hours prior to dosing and standard meals are served 4.5, 12, 15, 24 and 28.5 hours after dosing. The intake of fluids is controlled from two hours prior to dosing until 4.5 hours after dosing. At the scheduled dosing time, subjects receive one oral dose (1 capsule or tablet) of the test formulation and reference according to a randomization schedule. Each dose is taken with 240 ml of tap water at room temperature. Blood samples are collected into Vacutainer® tubes containing Li Heparin prior to dosing then at 0.5, 1.0, 1.5, 2.0, 2.5, 3.0, 4.0, 5.0, 6.0, 8.0, 10, 12, 15, 18, 21, 24, 27, 30, 33 and 36 hours after dosing. Nifedipine concentrations are determined in plasma samples using a validated GC method. The LOQ of the assay is 1 ng/ml.

The present formulations tested in the human study correspond to the formulation of Example 2, except that each contains the following percentage of nifedipine: Test 1 (25% nifedipine); Test 2 (17% nifedipine); Test 3 (10% nifedipine); and Test 4 (a mixture of Test 1 and Test 3 to achieve an overall 17% nifedipine). Each formulation was prepared exactly as described in Example 5 except for the use of lower amounts of the pretreated nifedipine-CMC material. A sub-therapeutic extended release dose of total of 20 mg of nifedipine was administered to each subject. The reference formulation contained 30 mg of nifedipine.

Figure 8:
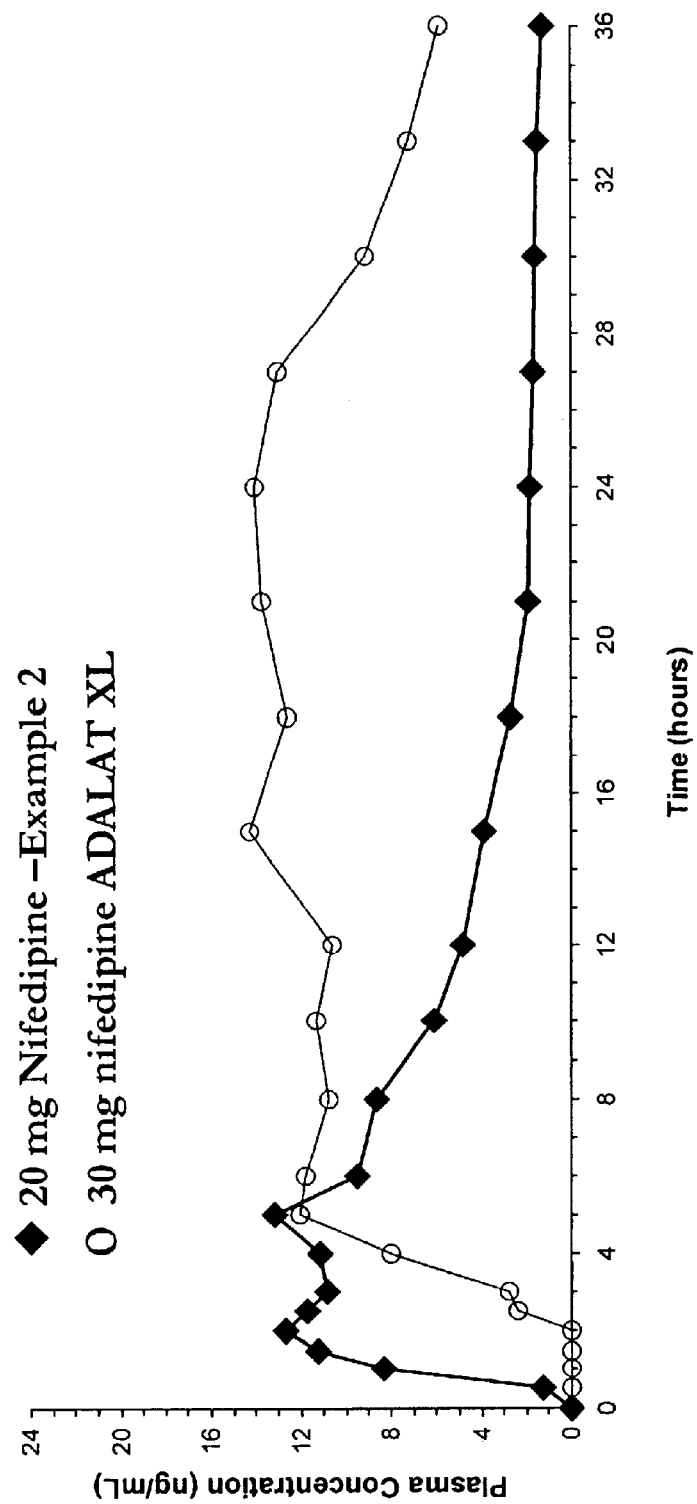
FIG. 8. is a graph showing the mean plasma levels achieved over time in a human study with the formulation prepared as described in Example 1 in comparison to the profile achieved with ADALAT XL, an osmotic delivery system.
Figure 9:
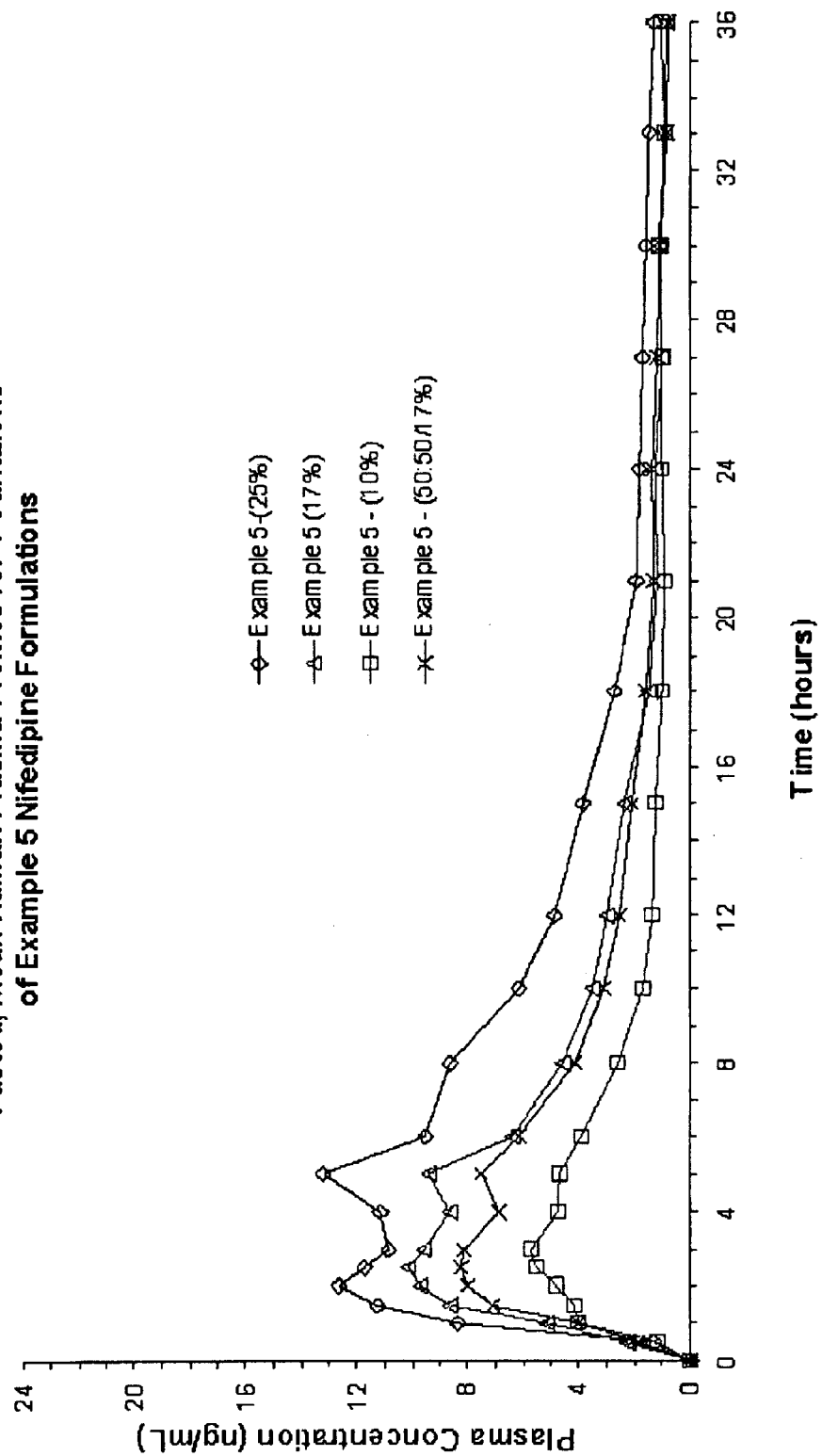
FIG. 9. is a graph showing the mean plasma levels achieved over time in a human study with four formulations of the invention wherein the only difference between the formulations is the loading percentage of the nifedipine used in the processing of the formulations.

The plasma levels of the four test formulations and the ADALAT XL product are presented graphically in FIGS. 8 and 9. The reference formulation, ADALAT XL® is an osmotic formulation that has a delayed onset beginning at about 3 hours, a mean plasma level that reaches about 12 ng/ml at 5 hours and continues at about that level for up to about 28 hours.

FIG. 9 shows that the rate of nifedipine buildup in the plasma differed among all formulations: the rate was greatest in the 25% formulation, intermediate in the two 17% formulations and lowest in the 10% formulation. The $T_{max}$ was delayed from 2 hr (25% load) to 2.5 hr (17% loads) to 3 hr (10% load), respectively. The second peaks at 5 hours corresponds to additional lipase activity generated as the result of a meal taken at 4.5 hours by each subject, indicating the residual presence of each formulation in the small intestine more than four hours after dosage. In each of the test formulations, nifedipine plasma levels could be measured at and beyond 24 hours.

Each of the test formulations administered in the human study included a matrix designed for enzymatic degradation by lipase secreted in the upper portion of the small intestine. Each formulation released its nifedipine in the small intestine within the first eight hours of the study, the majority of which appears to have been released between hours 1 and 6. The slower uptake of the lowest-loaded formulations is likely to be the result of a larger particle size of nifedipine resulting from insufficient particle size reduction and/or the greater amounts of Sterotex in the microsphere delaying the release of the nifedipine. The nifedipine particles that continue the intestinal transit into the large intestine appear to be very slowly absorbed, either due to their large size and insolubility and/or their encapsulation with undigested Sterotex.

It is believed that the relative bioavailability of the formulations reflects the particle size difference in the formulations and/or higher concentration of matrix material that is not digested or dispersed in the small intestine as noted above. The calculated amounts of nifedipine absorbed in the study are presented in the Table 5 below, where the measured value have been adjusted to reflect the administration of 30 mg per dose.

TABLE 5

NIFEDIPINE AUC (0-36 H) NORMALIZED TO A 30 MG SINGLE DOSE

| FORMULATION | AUC (mean) | AUC (median) | STDEV |
|---|---|---|---|
| TEST 1 (25%) | 230 | 211 | 96 |
| TEST 2 (17%) | 152.5 | 161 | 26 |
| TEST 3 (10%) | 78 | 66 | 33.5 |
| TEST 4 (50/50-17%) | 131 | 131 | 40.5 |
| REFERENCE (ADALAT XL) | 369.5 | 386 | 85.6 |

The AUC (non-normalized) of the Test 1 formulation (25% nifedipine) is 153+/−42%. Table 6 below shows that the AUC for Test 1 formulation is equivalent that of a 20 mg sustained release nifedipine formulation reported in the literature, but exhibits a first Tmax one hour delayed relative to that of the literature formulation.

| Reference | Subjects n | Dose (mg) | Cmax (ng/mL) | Tmax (hr) | $AUC_{0-t}$ (ng · mL/hr) | t1/2 (hr) |
|---|---|---|---|---|---|---|
| *Rawashdeh | Healthy male | 22 | 10 mg IR tablet | 108 (74–159) 117 (81–171) | — — | 207 (139–308), 0–10 hr 210 (135–327), 0–10 hr | 2.31 (1.78–3.02) 2.27 (1.81–2.86) |
| **Sigusch | Healthy male | 10 | 20 mg SR tablet | 27 ± 41% 54 ± 37% § | 1.1 ± 55% 1.9 ± 42% § | 162 ± 52%, 0–24 hr 328 ± 44% §, 0–24 hr | 5.3 ± 30% 5.1 ± 24% § |

IR - Immediate release, SR - Slow release, § - Tablet administered with grapefruit juice,
References:
(*Rawashdeh NM, Battah AH, Irshaid YM and Al-Qato MK, Eur. J. Drug Metab. Pharmacokinet., 3 (1997) 259–264. Comparative pharmacokinetics of two nifedipine products in capsule form following single oral administration in healthy volunteers.);
(**Sigusch H, Hippius M, Henschel L, Kaufmann K and Hoffmann A, Pharmazie 49 (1994) 522–524. Influence of grapefruit on the pharmacokinetics of a slow release nifedipine formulation.).

Example 3

Microspheres of Nifedipine/Pectin-CMC Microcapsules in a Matrix of Polymorphic Wax Preparation of nifedipine/pectin-containing microcapsules: Disperse 1.34% w/w of milled nifedipine (<10 micron) into an aqueous solution of 3% w/w of pectin (LM 208, Degussa Texturant, Baute, France) and 0.66% w/w Na CMC in 1000 mls of water. Subject the aqueous dispersion to a pressure-force by passing it three times through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacer with a length of about 0.04 in and a diameter of about 0.25 in, a baffle plate consisting of 4 holes (0.02 in ID), a second spacer, and an exit nozzle consisting of four holes (0.02 in ID). The pressure-treated mixture is then sprayed in a fine mist of aqueous nifedipine/pectin particles (mean size of about 50 microns) into a rapidly strong aqueous solution of 30% $CaCl_2$ (calcium chloride dihydrate (Merck, Darmstadt, Germany)) and allowed to stand after addition for 10 minutes. The resulting cross-linked pectin microcapsules are collected with vacuum filtration, the filtrate rinsed with distilled water, and oven dried at 45° C., yielding about 50 grams of dry nifedipine/pectin-containing microcapsules.

Preparation of nifedipine/CMC-containing microcapsules: Milled nifedipine (195 g; <10 micron) is dispersed in an aqueous solution of Na CMC (97.5 g) (in 2.7 liters of distilled water) using a high speed homogenizer (Silverson homogenizer, Model No. L4RT at 8000 rpm). After addition, stirring is continued for about 10 min at 9500 rpm. The dispersion is stored in a container protected from exposure to light. The homogenized mixture is then spray dried (Bowen Industries Co., spray dryer—30 inch diameter lab unit, 0.125 mm diameter nozzle from Spray Systems Inc.) at 300° F. inlet and 213° F. outlet, using 60 psi air pressure and a feed rate of 60 ml/min. (peristaltic pump) resulting in fine particles of nifedipine/CMC material.

Preparation of the Microcapsule Matrix: Add 50 grams of the dry nifedipine/pectin microspheres and 5 grams of the nifedipine/CMC particles in a melt of 112 grams of Sterotex, NF at 75 C. Subject the Sterotex dispersion to a pressure-force by passing it three times through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacer with a length of about 0.04 in and a diameter of about 0.25 in, a baffle plate consisting of 4 holes (0.02 in ID), a second spacer, and an exit nozzle consisting of four holes (0.02 in ID). The pressure-treated mixture is sprayed through an air-atomizing nozzle maintained at 123 degrees C., from a closed vessel with top displacement air pressure of 2 psi, aspirator pressure of 10 psi, into a temperature-chilled chamber. All work is done in a red light environment. The resulting microsphere material is capable of passing through the acidic environment of the stomach without releasing nifedipine, releasing nifedipine in a first controlled manner by digestion of the Sterotex upon contact with lipase and surfactant in the small intestine, and upon passing into the large intestine, releasing further nifedipine in a sustained manner upon digestion of the pectin component of the microcapsules released from the waxy matrix in the small intestine.

We claim:

1. A microsphere comprising a water insoluble organic matrix containing (a) an interior region comprising a plurality of microcapsules consisting essentially of a core of bioactive compound coated with material containing charged organic groups, and (b) a surface region substantially free of said bioactive compound.

2. The microsphere of claim 1, wherein said microsphere has a diameter of from about 10 microns to about 1000 microns.

3. The microsphere of claim 2, where said microspheres are substantially spherical and have a mean particle size of from about 20 to about 800 microns.

4. The microsphere of claim 1, wherein said microcapsules contain cores having a diameter of less than about ten microns.

5. The microsphere of claim 4, wherein said cores comprise solid particles.

6. The microspheres of claim 4, wherein said cores are fluid.

7. The microsphere of claim 4, wherein said cores are water soluble, sparingly soluble in water or water insoluble.

8. The microsphere of claim 1, wherein said material comprises an anionic or cationic polymer.

9. The microsphere of claim 8, wherein said polymer consists essentially of a polymeric backbone to which a plurality of pharmaceutically acceptable alkyl carboxylic acid or sulfate addition salts are covalently bonded.

10. The microsphere of claim 9, wherein said polymer backbone is selected from the group consisting of cellulose, hemicellulose, galactose polymer and 3,6-anhydrogalactose copolymers.

11. The microsphere of claim 10, wherein said polymer backbone is cellulose.

12. The microsphere of claim 10, wherein said polymer is a pharmaceutically acceptable monovalent salt of an anionic polymer selected from the group consisting of carboxyalkylcellulose, pectinate, carrageenenate, xanthanate and alginate.

13. The microsphere of claim 12, wherein said salt is an alkali metal or ammonium salt.

14. The microsphere of claim 13, wherein said polymer salt further comprises an amount of di- or tri-valent cation salt.

15. The microsphere of claim 1, wherein said water insoluble matrix comprises a pH insensitive material.

16. The microsphere of claim 15, wherein said pH insensitive material comprises a member selected from the group consisting of triglycerides, hydrogenated vegetable oils, a wax or a mixture of waxes, triglycerides, polyalkoxyalkylethers, polyalkoxyalkylesters and water insoluble partially-degraded proteins.

17. The microsphere of claim 16, wherein said pH insensitive material comprises a partially digestible wax.

18. The microsphere of claim 17, wherein said pH insensitive material further comprises from 0 to about 50 wt % of a water insoluble polysaccharide, a polyethylene glycol or glycol ether, or an indigestible wax.

19. The microsphere of claim 17, wherein said material comprises from about one to about 50 wt % of an aliphatic alcohol having from about 8 to about 20 carbon atoms, based on the weight of the total material.

20. The microsphere of claim 19, wherein said alcohol is a fatty acid alcohol.

21. The microsphere of claim 20, wherein said alcohol is cetyl alcohol.

22. A pharmaceutical composition comprising microspheres, each having a surface and an interior, and comprising a pharmaceutically acceptable water insoluble organic matrix material, within which interior are distributed water-dispersable capsules consisting essentially of a core of a bioactive compound in a pharmaceutically effective amount, said core having a mean particle size of less than about ten microns in diameter and having a coating consisting essentially of an organic material having multiple charged groups, wherein said capsules are distributed homogenously within said microsphere.

23. The pharmaceutical composition of claim 22, wherein said microspheres have a mean diameter of from about 20 microns to less than about one millimeter.

24. The pharmaceutical composition of claim 22, wherein said water insoluble organic matrix material melts between about 120 degrees F. and about 225 degrees F.

25. The pharmaceutical composition of claim 22, wherein said water insoluble matrix material comprises a component that is digestible by enzymes present in the human intestinal tract.

26. The pharmaceutical composition according to claim 22 wherein said bioactive compound exhibits low permeability.

27. A pharmaceutical composition comprising microspheres having a structure of an outer surface, and an interior comprising matrix of pharmaceutically acceptable water insoluble material and microcapsules of a hydrophobic bioactive compound coated with a pharmaceutically acceptable charged hydrophilic material, which particles are distributed homogenously within said interior region and are absent from said surface.

28. The pharmaceutical composition of claim 27, wherein said hydrophobic particles are sparingly soluble to water insoluble.

29. The pharmaceutical composition of claim 28, wherein said hydrophilic material comprises an anionic or cationic polymeric material.

30. The pharmaceutical composition of claim 29, wherein said polymer is mucoadhesive.

31. The pharmaceutical composition of claim 30, wherein said polymer consists essentially of a polymeric backbone to which a plurality of pharmaceutically acceptable alkyl carboxylic acid or sulfate addition salts are covalently bonded.

32. The pharmaceutical composition of claim 31, wherein said polymer backbone is selected from the group consisting of cellulose, hemicellulose, galactose polymer and 3,6-anhydro-galactose copolymers.

33. The pharmaceutical composition according to claim 32 wherein said polymer backbone is cellulose.

34. The pharmaceutical composition according to claim 29 wherein said polymer is a pharmaceutically acceptable monovalent salt of an anionic polymer selected from the group consisting of carboxyalkylcellulose, pectinate, carrageenenate, xanthanate and alginate.

35. The pharmaceutical composition according to claim 34 wherein said salt is an alkali metal or ammonium salt.

36. The pharmaceutical composition according to claim 35 wherein said polymer salt further comprises an amount of di- or tri-valent cation salt.

37. The pharmaceutical composition according to claim 27 wherein said water insoluble material comprises a pH insensitive material.

38. The pharmaceutical composition according to claim 37 wherein said pH insensitive material is digestible by enzymes present in the human intestinal tract.

39. The pharmaceutical composition according to claim 38 wherein said pH insensitive material comprises one or more components digestible by enzymes present in the small intestine.

40. The pharmaceutical composition according to claim 39 wherein said components are digestible by lipases present in the small intestine.

41. A pharmaceutical composition according to claim 40 wherein said material comprises a member selected from the group consisting of triglycerides, hydrogenated vegetable oils, triglyceride polyalkoxyalkylesters and water insoluble partially-degraded proteins.

42. A pharmaceutical composition according to claim 41 wherein said material further comprises from 0 to about 50 wt % of an aliphatic alcohol having from about 8 to about 20 carbon atoms, based on the weight of the total material.

43. A pharmaceutical composition according to claim 42 wherein said alcohol is a fatty acid alcohol.

44. A pharmaceutical composition according to claim 43 wherein said alcohol is cetyl alcohol.

45. A pharmaceutical composition according to claim 39 wherein said material further comprises from 0 to about 50 wt % of a long-lasting material that is indigestible by enzymes in the human small intestine.

46. A pharmaceutical composition according to claim 45 wherein said long-lasting material comprises a water insoluble polysaccharide, a polyethylene glycol or glycol ether, or an indigestible wax.

47. A pharmaceutical composition according to claim 46, wherein said long-lasting material comprises a material that is digestible by enzymes present in the large intestine.

48. A method for administering a sustained-release pharmaceutical composition containing bioactive compound to a patient in need thereof, comprising administering to said subject a pharmaceutically effective amount of composition according to claim 23.

49. A method according to claim 48 wherein said compound is released to said patient from said composition over a period of time of from about 8 to about 36 hours.

50. A method according to claim 49 wherein said composition is contacted with a subject membrane capable of absorbing said bioactive compound.

51. A process for the production of pharmaceutically acceptable microspheres comprising spraying, into a chilling zone, a flowable dispersion of bioactive micron-sized organic particles containing charged organic moieties in a water insoluble fluid matrix, under conditions that form droplets of said dispersion, and maintaining the fluidity of said droplets for a time sufficient to distribute homogenously said particles within said droplets, and allowing said droplets to solidify into said microspheres.

52. The process of claim 51 wherein the microspheres are sprayed under pressure.

53. The process of claim 52 wherein said microspheres are sprayed through an electrically charged spray nozzle.

54. The process of claim 51 wherein said bioactive particles contain anionic organic groups.

55. The process of claim 54 wherein said particles contain a pharmaceutically acceptable, water-soluble polyanionic polymer.

56. The process of claim 55 wherein said polymer consists essentially of a polymeric backbone to which a plurality of pharmaceutically acceptable alkyl carboxylic acid addition salts or alkyl phosphate acid addition salts are covalently bonded.

57. A process according to claim 51 wherein said matrix comprises one or more water insoluble components.

58. The process of claim 57 further comprising the step of first subjecting a dispersion of bioactive organic particles and a water soluble organic material containing charged organic moieties in a water insoluble fluid medium to sufficient high-pressure forces to form said flowable dispersion of bioactive micron-sized organic particles.

59. The process according to claim 58 wherein said pressure force is applied to said dispersion of bioactive organic particles having a mean particle diameter size of greater than ten microns.

60. The process according to claim 58 wherein said high-pressure forces comprise compression, shear and cavitation forces.

61. A process according to claim 60 wherein said pressure force is applied for less than a second at a pressure of from about 2,000 psi to about 20,000 psi.

62. A process according to claim 61 wherein said pressure force is applied to said mixture which is passed through a chamber that subjects said mixture to cavitation and/or shear forces.

63. A microsphere according to claim 4 wherein said core particle is a water soluble solid.

64. A microsphere according to claim 63 wherein said core particle is embedded in an aqueous gel of charged organic material.

65. A microsphere according to claim 64 wherein the concentration of said material in said gel is high enough to prevent dissolution of said core particle in said gel.

66. A microsphere according to claim 65 wherein said concentration is between about 40 to about 95 percent by weight.

67. A microsphere according to claim 66 wherein said particle is a low permeability pharmaceutical compound.

68. A process according to claim 67 wherein said dispersion comprises a micro-dispersion consisting essentially of highly concentrated aqueous gel of said charged organic material.

69. A process according to claim 68 wherein said flowable dispersion is homogenized with a water-in-oil emulsion of an aqueous solution of a multivalent cationic salt of a bioenhancer in said water insoluble fluid medium, said dispersion containing a pharmaceutically acceptable, water soluble polyanionic polymer, and thereby forming a flowable dispersion of bioactive organic particles encapsulated with a cross-linked moisture-containing polyanionic polymer.

* * * * *